United States Patent [19]

Battles et al.

[11] Patent Number: 5,423,783
[45] Date of Patent: Jun. 13, 1995

[54] OSTOMY BAG WITH ELASTIC AND HEAT SEALABLE MEDICAL TAPES

[75] Inventors: Donald R. Battles, Arden Hills; Eugene G. Joseph, Vadnais Heights; Audrey S. Huang, Arden Hills; John F. Reed, North Oaks; Scott M. Purrington, Maplewood, all of Minn.

[73] Assignee: Minnesota Mining and Manufacturing Company, St. Paul, Minn.

[21] Appl. No.: 219,216

[22] Filed: Mar. 29, 1994

Related U.S. Application Data

[63] Continuation-in-part of Ser. No. 37,902, Mar. 26, 1993, Pat. No. 5,316,838, which is a continuation-in-part of Ser. No. 768,173, Sep. 30, 1991, Pat. No. 5,238,733.

[51] Int. Cl.⁶ ............................................. A61F 5/44
[52] U.S. Cl. ............................................... 604/344
[58] Field of Search ............................ 604/344, 339

[56] References Cited

U.S. PATENT DOCUMENTS

| | | | |
|---|---|---|---|
| 2,910,065 | 10/1959 | Mavsan | 604/344 |
| 3,480,502 | 11/1969 | Schrenk | 156/271 |
| 3,487,505 | 1/1970 | Chisholm et al. | 18/13 |
| 3,557,265 | 1/1971 | Chisholm et al. | 264/47 |
| 3,645,835 | 2/1972 | Hodgson | 161/146 |
| 3,687,589 | 8/1972 | Schrenk | 425/109 |
| 3,759,647 | 9/1973 | Schrenk et al. | 425/131 |
| 3,825,379 | 7/1974 | Lohkamp et al. | 425/72 |
| 3,849,241 | 11/1974 | Butin et al. | 161/169 |
| 3,897,780 | 8/1975 | Trousil | 604/344 |
| 3,924,990 | 12/1975 | Schrenk | 425/131.1 |
| 3,971,373 | 7/1976 | Braun | 128/146.2 |
| 4,118,531 | 10/1978 | Hauser | 428/224 |
| 4,197,069 | 4/1980 | Cloerem | 425/131.1 |
| 4,429,001 | 1/1984 | Kolpin et al. | 428/283 |
| 4,477,516 | 10/1984 | Sugihara et al. | 428/296 |
| 4,547,420 | 10/1985 | Krueger et al. | 428/229 |
| 4,681,574 | 7/1987 | Eastman | 604/344 |
| 4,710,190 | 12/1987 | Wood et al. | 604/389 |
| 4,755,178 | 7/1988 | Insley et al. | 604/367 |
| 4,871,812 | 10/1989 | Lucast et al. | 525/186 |
| 4,908,263 | 3/1990 | Reed et al. | 428/286 |
| 4,919,999 | 4/1990 | Van Soom | 428/284 |
| 4,957,795 | 9/1990 | Riedel | 428/74 |
| 4,973,323 | 11/1990 | Kaczmarek et al. | 604/339 |
| 5,026,591 | 6/1991 | Henn et al. | 428/198 |
| 5,139,492 | 8/1992 | Leise, Jr. et al. | 604/339 |
| 5,230,701 | 7/1993 | Meyer et al. | 602/76 |
| 5,238,733 | 8/1993 | Joseph et al. | 428/284 |

FOREIGN PATENT DOCUMENTS 0366379 2/1990 European Pat. Off.

Primary Examiner—Jerome L. Kruter
Attorney, Agent, or Firm—Gary L. Griswold; Walter N. Kirn; F. Andrew Ubel

[57] ABSTRACT

The present invention provides a medical tape comprising a highly conformable and deformable nonwoven web coated with an adhesive. The non-adhesive side of the web may be heat bonded to many different polymeric film materials and is particularly useful with ostomy pouch films. The present invention also provides ostomy bags comprising an elastic, breathable nonwoven based medical tape.

16 Claims, 6 Drawing Sheets

OSTOMY BAG WITH ELASTIC AND HEAT SEALABLE MEDICAL TAPES

This is a continuation-in-part of U.S. patent application Ser. No. 08/037,902, now U.S. Pat. No. 5,316,838 filed Mar. 26, 1993, which is a continuation-in-part of Ser. No. 07/768,173 now U.S. Pat. No. 5,238,733, filed Sep. 30, 1991.

FIELD OF THE INVENTION

The invention relates to a medical tape comprising a highly conformable and deformable nonwoven web coated with an adhesive. The tape is heat bondable to a variety of polymer substrates and has particular utility when used, for example, in the construction of ostomy appliances. The invention also relates to conformable or stretchable nonwoven webs useful as backings for medical tapes and the methods for their production.

BACKGROUND OF THE INVENTION

In one embodiment, the present invention relates to ostomy appliances and in particular to medical tapes used to attach an ostomy appliance to a body. An ostomy appliance is a device used to collect waste material that exits a person's body through a stoma. The term "stoma" refers to the surgically created hole in the skin and the attached end of the bladder, conduit, or intestine. The stoma provides an open conduit through which a constant or intermittent efflux of waste material occurs. The surrounding skin area is termed the "peristomal area." A great challenge exists to comfortably and reliably connect an ostomy appliance to the peristomal area.

Currently, tapes used for securing medical devices such as an ostomy pouch to a patient are formed from generally non-elastic nonwoven webs or plastic films or webs which cannot be directly heat bonded to the ostomy appliance. Plastic films are often used where protection of the underlying skin from moisture, urine or fecal material is critical. Unfortunately, the most common plastic films used for this application are essentially impermeable to moisture vapor, and do not allow the skin to "breathe."

Cymed, Inc. (Hayward, Calif.) manufactures an ostomy pouch comprising a urethane film tape for securing the pouch to the skin. However, this film tape is not porous (hence its moisture vapor transmission rate is lower than optimally desired). In addition, the urethane film is only heat bondable to other urethane surfaces, and therefore, requires a separate means of bonding the tape to the pouch. U.S. Pat. No. 4,681,574 (Eastman) is believed to generally describe this type of ostomy pouch.

It would be desirable to have a medical tape that is suitable for directly securing a medical device to a patient's skin. The tape should be suitable for long term wear on skin (e.g., have high moisture vapor transmission rate, air porosity, elasticity and conformability) and should also be suitable for directly securing to the ostomy bag (e.g., have heat bondability with an ostomy bag film).

SUMMARY OF THE INVENTION

This invention consists of an elastic nonwoven web (incorporating at least two components) coated with adhesive, suitable for use as a medical tape. The elastic nonwoven web is additionally heat or sonically bondable (also referred to as "heat sealable") to typical materials used in ostomy pouch films. The elastic nonwoven webs of the present invention comprise blown microfibers formed by extrusion of thermoplastic elastomers through a die which produces fine, randomly oriented fibers. Several different constructions of webs are suitable for use in this invention. In a first embodiment the elastic nonwoven web comprises longitudinally layered melt-blown microfibers, comprising layers of a low modulus or elastomeric material and adjacent layers of a heat bondable material which will enable the web to be heat bonded to typical ostomy appliance films. In a second embodiment the elastic nonwoven web comprises at least two different types of melt-blown microfibers. A first microfiber comprises a low modulus or elastomeric material; a second microfiber comprises a heat bondable material which will enable the web to be heat bonded to typical ostomy appliance films. In a third embodiment an elastomeric nonwoven web is produced using an elastomeric blown microfiber and a larger-diameter staple fiber which will enable the web to be heat bonded to typical ostomy appliance films. The elastomeric microfibers and staple fibers of the resulting web are generally randomly intermixed and intertangled. In all three embodiments the combination of an elastomer and a heat bondable material provide webs which are elastomeric, yet heat bondable to many different polymeric films.

The tapes of the present invention have application as a medical tape in areas requiring conformability and/or elasticity, and where long term wear is desirable. The tapes of the present invention possess good moisture vapor transmission, and therefore, allow more natural skin function. This feature allows the tape to be worn tier longer periods of time than typical more occlusive tapes.

One specific application that this tape appears to be highly suited for is as a tape used to secure ostomy pouches to the skin. Ostomies are located on the abdomen, and there/ore, require a tape that will both conform to the abdominal contours and move (or stretch) with the skin as the skin moves. Further, the tape used on ostomy pouches must be fastened to the pouch film in some manner, often by heat sealing the film and tape layers together. The tapes of the present invention can be directly sealed to typical ostomy pouch films and do not require an additional layer to form a seal to the pouch. The present tape constructions can be sterilized by gamma irradiation, with no loss to or only minimal effect on tape properties. This feature is a highly desirable attribute of medical tapes and specifically tapes used to secure ostomy pouches to the peristomal region immediately after surgery.

DETAILED DESCRIPTION OF THE INVENTION

The present invention provides a medical tape comprising an elastic nonwoven web, as herein disclosed, and an adhesive coated on at least one side of said web. The elastic nonwoven webs of the present invention comprise blown microfibers ("BMF") formed by extrusion of thermoplastic elastomers through a die which produces fine, randomly oriented fibers. Several different constructions of webs are suitable for use in this invention. More specifically, three alternative methods of producing the elastomeric web are disclosed. In a first embodiment ("multilayered blown microfibers"), the elastic nonwoven web comprises longitudinally layered melt-blown microfibers, comprising layers of a low modulus or elastomeric materials and adjacent layers of heat bondable materials. In a second embodiment ("commingled blown microfibers"), the elastic nonwoven web comprises at least two different types of melt-blown microfibers. A first microfiber comprises a low modulus or elastomeric material; a second microfiber comprises a heat bondable material. In a third embodiment ("blown microfiber web having intertangled staple fiber"), an elastomeric nonwoven web is produced using an elastomeric blown microfiber and a larger-diameter staple fibers. The elastomeric microfibers and staple fibers of the resulting web are generally randomly intermixed and intertangled. All three embodiments are heat bondable to typical films used in ostomy appliances.

Multilayered Blown Microfibers

In a first presently preferred embodiment, the elastomeric medical tape comprises a non-woven web of longitudinally layered melt-blown microfibers, comprising layers of a low modulus or elastomeric materials and adjacent layers of heat bondable materials. The microfibers are produced by a process comprising first feeding separate polymer melt streams to a manifold means, optionally separating at least one of the polymer melt streams into at least two distinct streams, and combining all the melt streams, including the separated streams, into a single melt stream of longitudinally distinct layers, preferably of at least two different polymeric materials arrayed in an alternating manner. The combined melt stream is then extruded through fine orifices and formed into a highly conformable and stretchable web of melt-blown microfibers.

Figure 1A:
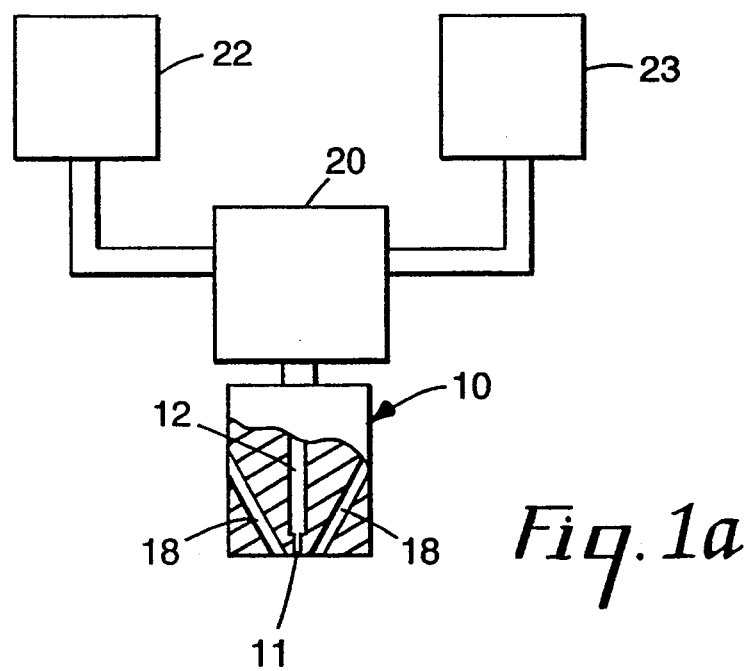
FIGS. 1a, 1b, and 1c are schematic views of apparatuses useful in the practice of the invention method.

The microfibers are produced, in part, using the apparatus discussed, for example, in Wente, Van A., "Superfine Thermoplastic Fibers," *Industrial Engineering Chemistry*, Vol. 48, pp 1342–1346 and in Wente, Van A. et al., "Manufacture of Superfine Organic Fibers," Report No. 4364 of the Naval Research Laboratories, published May 25, 1954, and U.S. Pat. Nos. 3,849,241 (Butin et al.), or 3,825,379 (Lohkamp et al.). These apparatuses and methods are useful in the invention process in the portion shown as die 10 in FIG. 1a, which could be of any of these conventional designs.

The polymeric components are introduced into the die cavity 12 of die 10 from a separate splitter, splitter region or combining manifold 20, and into the, e.g., splitter from extruders, such as 22 and 23. Gear pumps and/or purgeblocks can also be used to finely control the polymer flowrate. In the splitter or combining manifold 20, the separate polymeric component flowstreams are formed into a single layered flowstream. However, preferably, the separate flowstreams are kept out of direct contact for as long a period as possible prior to reaching the die 10. The separate polymeric flowstreams from the extruder(s) can be split in the splitter (20). The split or separate flowstreams are combined only immediately prior to reaching the die, or die orifices. This minimizes the possibility of flow instabilities generating in the separate flowstreams after being combined in the single layered flowstream, which tends to result in non-uniform and discontinuous longitudinal layers in the multi-layered microfibers. Flow instabilities can also have adverse effects on non-woven web properties such as strength, temperature stability, or other desirable properties obtainable with the invention process.

The separate flowstreams are also preferably established into laminar flowstreams along closely parallel flowpaths. The flowstreams are then preferably combined so that at the point of combination, the individual flows are laminar, and the flowpaths are substantially parallel to each other and the flowpath of the resultant combined layered flowstream. This again minimizes turbulence and lateral flow instabilities of the separate flowstreams in and after the combining process. It has been found that a suitable splitter 20, for the above-described step of combining separate flowstreams, is one such as is disclosed, for example, in U.S. Pat. No. 3,557,265, which describes a manifold that forms two or three polymeric components into a multi-layered rectilinear melt flow. The polymer flowstreams from separate extruders are fed into plenums then to one of the three available series of ports or orifices, each series of ports is in fluid communication with one of the plenums. Each stream is thus split into a plurality of separated flowstreams by one of the series of ports, each with a height-to-width ratio of from about 0.01 to 1. The separated flowstreams, from each of the three plenum chambers, are then simultaneously coextruded by the three series of parts into a single channel in an interlacing manner to provide a multi-layered flowstream. The combined, multi-layered flowstream in the channel is then transformed (e.g., in a coat hanger transition piece), so that each layer extruded from the manifold orifices has a substantially smaller height-to-width ratio to provide a layered combined flowstream at the die orifices with an overall height of about 0.13 cm or less, preferably 0.04 to 0.08 cm or less. The width of the flowstream can be varied depending on the width of the die. Other suitable devices for providing a multi-layer flowstream are such as disclosed in U.S. Pat. Nos. 3,924,990 (Schrenk); 3,687,589 (Schrenk); 3,759,647 (Schrenk et al.) or 4,197,069 (Cloeren), all of which, except Cloeren, disclose manifolds for bringing together diverse polymeric flowstreams into a single, multi-layer flowstream that is ordinarily sent through a coat hanger transition piece or neck-down zone prior to the film die outlet. The Cloeren arrangement has separate flow channels in the die cavity. Each flow channel is provided with a back-pressure cavity and a flow-restriction cavity, in successive order, each preferably defined by an adjustable vane. The adjustable vane arrangement permits minute adjustments of the relative layer thicknesses in the combined multi-layered flowstream. The multi-layer polymer flowstream from this arrangement need not necessarily be transformed to the appropriate length/width ratio, as this can be done by the vanes, and the combined flowstream can be fed directly into the die cavity 12.

The multi-layer polymer flowstream is normally fed into the die cavity 12 as an integral flow. However, it is possible to keep the layer flowstreams separate in the die cavity 12 by use of separator plates that would allow the separate polymer flowstreams to combine immediately prior to reaching the die orifices.

From the die cavity 12, the multi-layer polymer flowstream is extruded through an array of side-by-side orifices 11. As discussed above, prior to this extrusion, the feed can be formed into the appropriate profile in the cavity 12, suitably by use of a conventional coat hanger transition piece. Air slots 18, or the like, are disposed on either side of the row of orifices 11 for directing uniform heated air at high velocity at the extruded layered melt streams. The air temperature is generally about that of the meltstream. This hot, high-velocity air draws out and attenuates the extruded polymeric material, which will generally solidify after traveling a relatively short distance from the die 10. The solidified or partially solidified fibers are then formed into a web by known methods and collected (not shown). The collecting surface can be a solid or perforated surface in the form of a flat surface or a drum, a moving belt, forming screen, or the like. If a perforated surface or screen is used, the backside of the collecting surface can be exposed to a vacuum or low-pressure region to assist in the deposition of fibers. The collector distance can generally be from 7 to 127 cm from the die face. With closer placement of the collector, the fibers are collected when they have more velocity and are more likely to have residual tackiness from incomplete cooling. This is particularly true for inherently more tacky thermoplastic materials, such as thermoplastic elastomeric materials. Moving the collector closer to the die face, e.g., preferably 7 to 30 cm, will result in stronger inter-fiber bonding and a less lofty web. Moving the collector back will generally tend to yield a loftier and less coherent web.

The temperature of the polymers in the splitter region is generally about the temperature of the higher melting point component as it exits its extruder. This splitter region or manifold is typically integral with the die and is kept at the same temperature. The temperature of the separate polymer flowstreams can also be controlled to bring the polymers closer to a more suitable relative viscosity. When the separate polymer flowstreams converge, they should generally have an apparent viscosity of from 150 to 800 poise (measured by a capillary rheometer). The relative viscosities of the separate polymeric flowstreams to be converged should generally be fairly well matched. Empirically, this can be determined by varying the temperature of the melt and observing the crossweb properties of the collected web. The more uniform the crossweb properties, the better the viscosity match. The overall viscosity of the layered combined polymeric flowstream(s) at the die face should be from 150 to 800 poise, preferably from 200 to 400 poise. The differences in relative viscosities are preferably generally the same as when the separate polymeric flowstreams are first combined. The apparent viscosities of the polymeric flowstream(s) can be adjusted at this point by varying the temperatures as per U.S. Pat. No. 3,849,241 (Butin, et al).

The size of the polymeric fibers formed depends to a large extent on the velocity and temperature of the attenuating airstream, the orifice diameter, the temperature of the melt stream, and the overall flow rate per orifice. At high air volume rates, the fibers formed have an average fiber diameter of less than about 10 micrometers. However, there is an increased difficulty in obtaining webs having uniform properties as the air flow rate increases. At more moderate air flow rates, the polymers have larger average diameters, however, with an increasing tendency for the fibers to entwine into formations called "ropes" or "bundles." This is dependent on the polymer flow rates, of course, with polymer flow rates in the range of 0.05 to 0.5 gm/min/orifice generally being suitable. Coarser fibers, e.g., up to 25 micrometers or more, can be used in certain circumstances such as large pore webs with high moisture vapor transmission.

The microfibers of this embodiment are formed from an elastomeric material forming one layer or layers and a heat bondable material forming the other layer or layers. Preferably, the heat bondable material forms at least one outer layer.

Low modulus or elastomeric material refers to any material that is capable of substantial elongation, e.g. preferably greater than about 100 percent, without breakage. At low stress levels, the Young's modulus is generally in the range from about $10^4$ to $10^7$ N/m$^2$. These materials are preferably elastomers which will substantially resume their shape after being stretched. Such elastomers will preferably exhibit permanent set of about 20 percent or less, preferably 10 percent or less, when stretched at moderate elongations, preferably of about 100 percent. Elastomers include materials or blends, which are capable of undergoing elongations, preferably of up to 400–800% and more at room temperatures.

The heat bondable material is generally a lower melting material capable of being coextruded with the elastomeric or low modulus material.

Webs formed from these multilayer fibers exhibit remarkable conformability, which is believed due to the extensibility of individual fibers in a coherent web structure under low levels of stress. Webs also exhibit a remarkable extensibility without the usual web breakage. This is believed to be attributable to a unique complimentary combination of properties from the individual layers in the multilayer fibers and from the interfiber relationships in the web as a whole. The preferably elastomeric low modulus layers allows one to lower the individual fiber composite modulus to a level that permits ready extensibility at relatively low stress levels. As such, when the web is tensioned, the applied stress will dissipate by elongation of individual fibers rather than concentrating at web weak points, which could result in fiber breakage and web failure.

Further, when the low modulus material is an elastomer it will have a tendency to resume its original shape after being elongated. This thus results in a tendency for the web to contract after being stretched. This web contraction has been found to vary significantly depending on the materials used in the elastomer layer and the lower melting heat bondable layer, the relative volume percent of the respective layers and the overall number of layers in the microfibers. Generally the most recovery is exhibited by webs formed of microfibers having a relatively low number of layers and a higher volume percent of the elastomer layer material. The individual fibers that exhibit recovery also are self-crimping, namely, the fibers tend to coil and recover into a springlike form.

The low modulus or elastomeric material can be any such material suitable for processing by melt blowing techniques. This would include polymers such as polyurethanes (e.g. "Morthane TM ", available from Morton International, Inc.); A-B block copolymers where A is formed of poly(vinyl arene) moieties such as polystyrene, and B is an elastomeric mid-block such as a conjugated diene or a lower alkene in the form of a linear di- or tri-block copolymer, a star, radial or branched copolymer, such as elastomers sold as "KRATON TM " (Shell Chemical Co..); polyetheresters (such as "Arnitel TM " available from Akzo Plastics Co.); or polyamides (such as "Pebax TM " available from Atochem Co.). Copolymers and blends can also be used. For example, A-B block copolymer blends as described in U.S. Pat. No. 4,657,802 are suitable where such block copolymers are preferably blended with polyalkylenes.

For extremely low modulus elastomers, it may be desirable to provide greater rigidity and strength. For example, up to 50 weight percent, but preferably less than 30 weight percent, of the polymer blend can be stiffening aids such as polyvinylstyrenes, polystyrenes such as poly(alphamethyl)styrene, polyesters, epoxies, polyolefins, e.g., polyethylene or certain ethylene/vinyl acetates, preferably those of higher molecular weight, or coumarone-indene resin.

Viscosity reducing materials and plasticizers can also be blended with the elastomers and low modulus extensible materials such as low molecular weight polyethylene and polypropylene polymers and copolymers, or tackifying resins such as Wingtack TM aliphatic hydrocarbon tackifiers available from Goodyear Chemical Company. Tackifiers can also be used to increase the adhesiveness of an elastomeric low modulus layer to a relatively nonelastic layer. Examples of tackifiers include aliphatic or aromatic liquid tackifiers, polyterpene resin tackifiers, and hydrogenated tackifying resins. Aliphatic hydrocarbon resins are preferred.

The heat bondable material is preferably a lower melting polymer than the elastomeric material. Suitable polymers include ethylene copolymers of vinyl acetate (EVA), methacrylate (EMA), methacrylic acid (EMAA), acrylic acid (EAA), octene, hexene, and propylene; and polyalkylenes, such as polyethylene or polypropylene. Also useful are certain slightly elastomeric materials such as some olefinic elastomeric materials such as some ethylene/propylene, or ethylene/propylene/diene˙ elastomeric copolymers or other ethylenic copolymers such as some ethylene vinyl acetates.

The heat bondable material provides the web with the capability of readily heat or sonic bonding to itself or other materials. A preferred material is disclosed in U.S. Pat. No. 4,710,190, the substance of which is incorporated by reference, which describes a blend of high and low molecular weight portion polymers. The blends of high and low molecular weight portions are blends that exhibit tackiness and bonding characteristics at temperatures in the range of 50° C. to 110° C. The high and low molecular weight portions can include ethylene- or propylene-based copolymers. Particularly preferred are copolymers with polar comonomers such as ethylene/vinyl acetate (EVA), or like materials (see, e.g., E.P.A. 366379 A2). Also usable are blends of EVA and tackifiers such as synthetic hydrocarbon resins. These materials exhibit good bonding to polyethylene-based polymers or copolymer films such as polyethylene or EVA films. Although not as preferred, other heat- or sonic-bondable materials can be used as the heat bondable layer, however, it is preferred that this material have a melting temperature at least about 15° C. below that of the elastomeric layer so that the web retains some open structure following heat bonding. Suitable materials would include polyethylene polymers and blends such as disclosed in U.S. Pat. No. 4,477,516.

Heat or sonically bondable materials often exhibit relatively high self-bonding characteristics under meltblowing conditions and, as such, form very coherent webs without the elastomeric (or low modulus) material. Webs formed from these combinations of materials can be concentrically layered (e.g., sheath-core-type layering) with the heat sealable or sonically sealable material as the external sheath layer and exhibit some of the properties of the longitudinally layered embodiments.

Fiber coiling and occasional separation of individual outer layers from stressed fibers also results in a relatively high degree of lofting in the resultant web. This lofting yields an improved softness or feel to the web, making it desirable for use in applications where it may make skin contact such as medical tape backings.

In certain embodiments, the elastic recovery of stretched webs can be enhanced by heating the web. This heat-activated recovery can be used to advantage to create a heat-shrink elastic nonwoven web product for use in a wide variety of applications, particularly when this is coupled with the conformable nature of the web.

A property of the invention web when stretched and allowed to recover is the directionality of the resulting web's elasticity. The web will exhibit elastic properties substantially only in the direction the web is stretched. The elasticity is also limited by the point to which the web was originally stretched. The elastic behavior and loft of the web can thus be controlled to an appropriate level, depending on the application. For example, for bandage backings, a limited level of elasticity is all that is required. This desired level of elasticity could be obtained by adjusting the number of layers in the microfibers, the relative percent of the at least two layers (one of which is an elastomeric layer) or the degree or direction of elongation or stretch. A low degree (e.g., less than 50%) of elasticity is thus obtainable for uses such as medical wraps, bandages and the like. Higher degrees of elasticity (e.g, greater than 50%) are also obtainable.

As previously discussed, the web when stretched also displays a noted lofting effect, which is dependant to some degree on the amount of recovery. This loft is highly desirable for medical type uses. The increased loft will increase the web softness, breathability and wicking ability.

A further feature of the invention webs is an ability for the webs to undergo further recovery when heated generally to a temperature greater than about 60° C. This is useful for typical heat shrink applications for elastic films.

Fiber and web strength can be controlled within wide ranges for given combinations of polymers by varying, independently, the relative ratios of the polymers, the layer order in the microfibers, the number of layers, the collector distance and other process variables. The invention thus allows precise control of web strength by varying one or all of these variables.

Theoretically, for webs formed from the above described two types of layers either one can advantageously comprise 1 to 99 volume percent of the total fiber volume, however, preferably the heat bonding material will comprise at least about 10% of the fiber volume, more preferably at least 20% of the fiber volume. At the low end of this volume range, the heat bondable layers will still contribute significantly to the surface properties of the fibers forming the web without significantly modifying the bulk fiber properties, such as tensile strength, modulus behavior, and elasticity. In this manner, the polymers with desirable bulk properties, such as elasticity, can be combined with materials having desirable surface properties, such as good bondability, to provide melt-blown webs with a high relative proportion of the desirable properties from each polymer. At higher percentages, the heat bondable layers will still contribute disproportionately to fiber surface properties, but will contribute more to the fiber bulk properties.

With the invention, the web properties can also be altered by variations in the number of layers employed at a given relative volume percent and layer arrangement. As described above, variation in the number of layers, at least at a low number of layers, has a tendency to significantly vary the relative proportion of each polymer (assuming two polymeric materials) at the microfiber surface. This (assuming alternating layers of two polymeric materials) translates into variation of those web properties to which the microfiber surface properties significantly contribute. Thus, web properties can change depending on what polymer or composition comprises the outside layer(s). However, as the number of layers increases, this variation in web properties based on surface area effects diminishes. At higher-layer numbers, the relative thicknesses of the individual fiber layers will tend to decrease, significantly decreasing the surface area effect of any individual layer.

The webs formed can be of any suitable thickness for the desired end use. However, generally a thickness from 0.01 to 0.08 centimeters is suitable for most applications. Further, for some applications, the web can be a layer in a composite multi-layer structure. The other layers can be supporting webs and films (such as elastic films, semi-permeable films or impermeable films). Other layers could be used for purposes such as absorbency, surface texture, rigidification, etc. The other layers can be attached to the invention melt-blown web by conventional techniques such as heat bonding, binders or adhesives or mechanical engagement, such as hydroentanglement or needle punching.

The multi-layer microfibers of the invention can be admixed with other fibers or particulates prior to being collected. For example, sorbent particulate matter or fibers can be incorporated into the coherent web of blown multi-layered fibers as discussed in U.S. Pat. Nos. 3,971,373 or 4,429,001. In these patents, two separate streams of melt-blown fibers are established with the streams intersecting prior to collection of the fibers. The particulates, or fibers, are entrained into an airstream, and this particulate-laden airstream is then directed at the intersection point of the two microfiber streams. Other methods of incorporating particulates or fibers, such as staple fibers, staple fibers or binding fibers, can be used with the melt-blown multilayered microfiber webs, such as is disclosed, for example, in U.S. Pat. Nos. 4,118,531, 4,429,001 or 4,755,178, where particles or fibers are delivered into a single stream of melt-blown fibers.

Other materials such as surfactants or binders can be incorporated into the web before, during or after its collection, such as by use of a spray jet. If applied before collection, the material is sprayed on the stream of microfibers, with or without added fibers or particles, traveling to the collection surface.

Commingled Blown Microfibers

In a second embodiment ("commingled blown microfibers"), the elastic nonwoven web comprises at least two different types of melt-blown microfibers. A first microfiber comprises a low modulus or elastomeric material. A second microfiber comprises a heat bonding material. Each microfiber is separately formed by extruding either the elastomeric material or the heat bonding material through fine orifices. The apparatus used for the previous embodiment (without the splitter, splitter region or combining manifold) can be utilized. Notably, two extruders and two dies are employed. The two separate materials are each formed into microfibers from a meltstream using the previously discussed high-velocity airstream. This hot, high-velocity air draws out and attenuates the extruded polymeric materials, which will generally solidify after traveling a relatively short distance from the dies. The solidified or partially solidified fibers from each die are intersected prior to collection of the fibers (thus co-mingling the different microfibers) and then formed into a commingled web by known methods and collected as previously described.

The size of the polymeric fibers formed depends to a large extent on the velocity and temperature of the attenuating airstream, the orifice diameter, the temperature of the melt stream, and the overall flow rate per orifice. At high air volume rates, the fibers formed have an average fiber diameter of less than about 10 micrometers. Coarser fibers, e.g., up to 25 micrometers or more, can be used in certain circumstances such as large pore webs with high moisture vapor transmission.

Figure 1B:
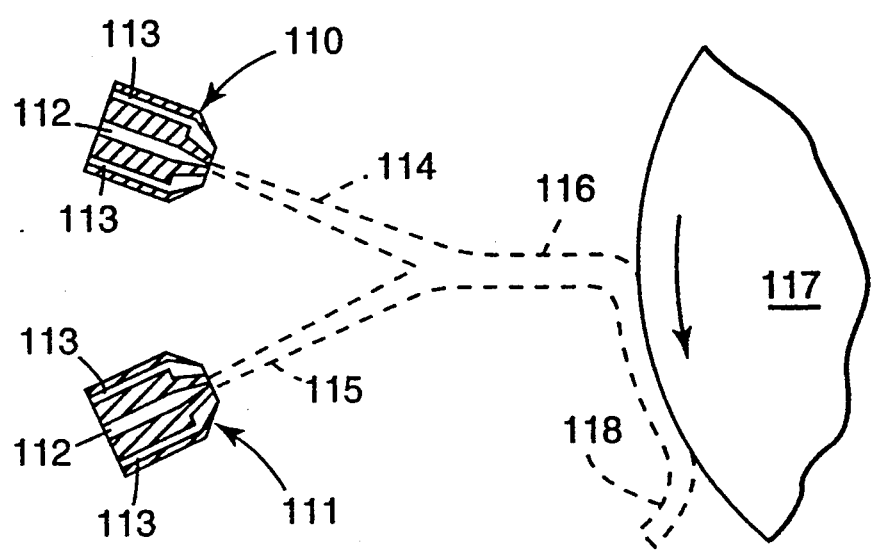

With reference to FIG. 1b, the illustrated apparatus includes two dies 110 and 111 which include a set of aligned parallel die orifices 112 through which the molten polymer is extruded, and cooperating air orifices 113 through which heated air is forced at very high velocity. The air draws out and attenuates the extruded polymeric material, and after a short travel in the gaseous stream, the extruded material solidifies as a mass of microfibers. According to this embodiment of the present invention, two dies are preferably used and arranged so that the streams 114 and 115 of microfibers issuing from them intersect to form one stream 116 that continues to a collector 117. The collecting surface can be a solid or perforated surface in the form of a flat surface or drum, a moving belt, forming screen, or the like. The collected web 118 of microfibers is then removed from the collector and processed as herein described.

The webs of this embodiment thus comprise at least two different types of microfibers. A first microfiber comprises a suitable low modulus or elastomeric material. The low modulus materials utilized in the previous embodiment (as part of the multilayered microfiber) are suitable for use in this embodiment. A second microfiber comprises a suitable heat bonding material. The heat bonding materials utilized in the previous embodiment (as part of the multilayered microfiber) are suitable for use in this embodiment. Notably, since these materials are not being coextruded as described in the first embodiment, there is no requirement that the two different types of materials be capable of being coextruded.

Webs formed from these commingled blown microfibers exhibit remarkable conformability and remarkable extensibility without the usual web breakage. This is believed to be attributable to a unique complimentary combination of properties from the individual microfibers and from the intrafiber relationships in the web as a whole. A property of the invention web when stretched and allowed to recover is the directionality of the resulting web's elasticity.

Fiber and web strength can be controlled within wide ranges for given combinations of polymers by varying, independently, the relative ratios of the microfibers, the collector distance and other process variables. The invention thus allows precise control of web strength by varying one or all of these variables.

Theoretically, for webs formed from the above described two types of microfibers either one can advantageously comprise 1 to 99 volume percent of the total fiber volume, however, preferably the heat bonding material will comprise at least about 10% percent of the fiber volume, more preferably at least 20% of the fiber volume. At the low end of this volume range, the heat bondable material will still contribute significantly to the surface properties of the web without significantly modifying the bulk properties of the web, such as tensile strength, modulus behavior and elasticity. In this manner, the polymers with desirable bulk properties, such as elasticity, can be combined with materials having desirable surface properties, such as good bondability, to provide melt-blown webs with a high relative proportion of the desirable properties from each polymer. At higher percentages, the heat bondable material will still contribute disproportionately to web surface properties, but will contribute more to the web bulk properties.

The webs formed can be of any suitable thickness for the desired end use. However, generally a thickness from 0.01 to 0.08 centimeters is suitable for most applications. Further, for some applications, the web can be a layer in a composite multi-layer structure. The other layers can be supporting webs and films (such as elastic films, semi-permeable films or impermeable films). Other layers could be used for purposes such as absorbency, surface texture, rigidification, etc. The other layers can be attached to the invention melt-blown web by conventional techniques such as heat bonding, binders or adhesives or mechanical engagement, such as hydroentanglement or needle punching.

The commingled blown microfibers of the invention can be admixed with other fibers or particulates prior to being collected. For example, sorbent particulate matter or fibers can be incorporated into the coherent web of blown multi-layered fibers as discussed in U.S. Pat. Nos. 3,971,373 or 4,429,001. In these patents, two separate streams of melt-blown fibers are established with the streams intersecting prior to collection of the fibers. The particulates, or fibers, are entrained into an airstream, and this particulate-laden airstream is then directed at the intersection point of the two microfiber streams. Other methods of incorporating particulates or fibers, such as staple fibers, staple fibers or binding fibers, can be used with the melt-blown multilayered microfiber webs, such as is disclosed, for example, in U.S. Pat. Nos. 4,118,531, 4,429,001 or 4,755,178, where particles or fibers are delivered into a single stream of melt-blown fibers.

Other materials such as surfactants or binders can be incorporated into the web before, during or after its collection, such as by use of a spray jet. If applied before collection, the material is sprayed on the streams of microfibers, with or without added fibers or particles, traveling to the collection surface.

Blown Microfiber Web having Intertangled Staple Fiber

In a third embodiment ("blown microfiber web having intertangled staple fiber"), the present invention is directed to a process for producing a non-woven web of an elastomeric melt-blown microfiber (generally less than 10 μm diameter) and a larger diameter heat bonding staple fiber. The larger diameter staple fibers are randomly and thoroughly intermixed and intertangled with the microfibers (as the microfibers are formed) and account for at least 10 weight percent of the fibers in the web, more preferably at least 20 weight percent.

Figure 1C:
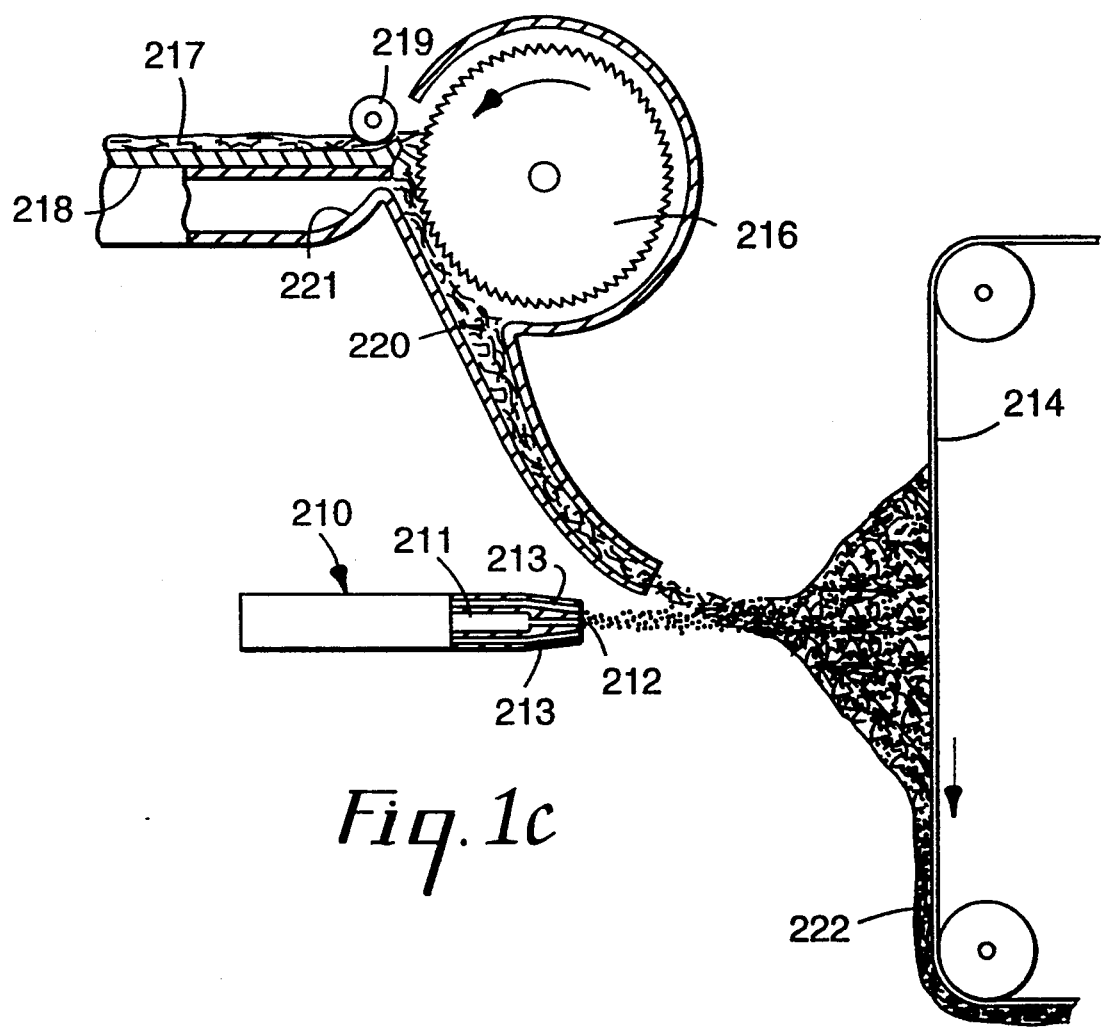

FIG. 1c of the drawing shows one arrangement of apparatus useful to prepare a web of the third embodiment. This apparatus prepares webs with melt-blown microfibers (prepared by extruding molten fiber-forming material and which are preferred in many webs of the invention). The melt-blowing portion of the illustrated apparatus can be a conventional structure as taught, for example, in Wente, Van A. "Superfine Thermoplastic Fibers", in Industrial Engineering Chemistry, Vol. 48, pages 1342 et seq (1956), or in Report No. 4364 of the Naval Research Laboratories, published May 25, 1954, entitled "Manufacture of Superfine Organic Fibers", by Wente, V. A., Boone, C. D., and Fluharty, E. L. Such a structure, illustrated in FIG. 1c, includes a die 210 which has an extrusion chamber 211 through which liquified fiber-forming material is advanced; die orifices 212 arranged in line across the forward end of the die and through which the fiber-forming material is extruded; and cooperating gas orifices 213 through which a gas, typically heated air, is forced at very high velocity. The high-velocity gaseous stream draws out and attenuates the extruded fiber-forming material, whereupon the fiber-forming material solidifies as microfibers during travel to a collector 214. The collecting surface 214 can be a solid or perforated surface in the form of a flat surface or a drum, a moving belt, forming screen, or the like. Gas-withdrawal apparatus may be positioned behind the screen to assist in deposition of fibers and removal of gas.

The staple fibers are introduced into the stream of blown microfibers in the illustrative apparatus shown in FIG. 1c through use of a lickerin roll 216 disposed above the microfiber-blowing apparatus. A web 217 of staple fibers, typically a loose, nonwoven web such as prepared on a card, garnet, or "Rando-Webber" machine, is propelled along a table 218 under a drive roll 219 where the leading edge engages against the lickerin roll 216. The lickerin roll turns in the direction of the arrow and picks off fibers from the leading edge of the web 217, separating the fibers from one another. The picked fibers are conveyed in an air stream through an inclined trough or duct 220 and into the stream of blown microfibers where they become mixed with the blown microfibers. The air stream is generated inherently by rotation of the lickerin roll, or that air stream may be augmented by use of an auxiliary fan or blower operating through a duct 221 as known in the art.

The mixed stream of microfibers and staple fibers then continues to the collector 214 where the fibers form a web 222 of randomly intermixed and intertangled fibers. Under close examination, the microfibers and staple fibers are found to be thoroughly mixed; for example, the web is free of clumps of staple fibers, i.e., collections a centimeter or more in diameter of many staple fibers. The web 222 is peeled off the collector, and typically wound into a storage roll. Subsequently, the web may be processed in cutting or handling operations appropriate for microfiber webs.

The composite web prepared may consist of a single layer deposited by apparatus as shown, or may be a multilayer product (in which the layers are typically indistinguishable to at least casual inspection). Such products can be formed either by passing the collected web under mixing and depositing apparatus such as illustrated in FIG. 1c two or more times or by having additional mixing and depositing apparatus disposed along the length of a collecting screen or belt.

The elastomeric melt blown small denier fibers can be prepared from the low modulus materials referred to earlier in the first and second embodiments. Preferably, the average diameter of the fiber is less than about 25 micrometers, more preferably between about 3 and 12 micrometers.

Suitable fibers for use as staple fibers in the nonwoven fabrics of the present invention include synthetic staple fibers such as, for example, monocomponent polyolefin fibers such as polypropylene, polyethylene, or olefin copolymers; "side-by-side" fibers comprising two layers of polymer (e.g., a polypropylene side and a polyethylene side); and "sheath-core" fibers comprising two annular layers of polymer (e.g., a polyethylene core and a polypropylene sheath). Preferred staple fibers are cut to a length between about 1 and 12 cm, more preferably between about 2 and 6 cm, most preferably between about 2.5 and 5 cm.

The staple fibers preferably have an average of more than about one half crimp per centimeter and, more preferably, have an average crimp frequency of at least two crimps per centimeter. As a minimum, the staple fibers should have an average length sufficient to include at least one complete crimp and preferably three to four crimps. The staple fibers preferably have an average length of between about 2 and 15 cm, more preferably between 3.5 to 8 cm.

The staple fibers preferably are at least about 0.5 denier, more preferably at least about 2 denier, most preferably about 3 denier, in size. Generally, the size of the staple fiber is no greater than about 15 denier, more preferably no greater than about 6 denier. Finer staple fibers provide more surface area for bonding (i.e., at the same volume fraction).

The nonwoven fabric of this embodiment contains about 10 to 90 weight percent elastomeric melt blown small denier fibers and 10 to 90 weight percent staple fibers, preferably 25 to 75 weight percent elastomeric melt blown small denier fibers and 25 to 75 weight percent staple fibers. The amount of staple fiber incorporated into the nonwoven stretch fabrics of the present invention depends on the particular use made of the web. As the amount of elastomeric melt blown small denier fiber increases, the strength and integrity, as well as the elasticity, of the fabric increases. When the amount of elastomeric melt blown small denier fibers is less than about 20 weight percent of the fabric, the strength and integrity of the fabric may be detrimentally affected.

Webs of all embodiments of the invention can be further processed after collection or assembly such as by calendaring or point embossing to increase web strength, provide a patterned surface, or fuse fibers at contact points in a web structure or the like; by orientation to provide increased web strength; by needle punching; heat or molding operations; coating, such as with adhesives to provide a tape structure, or the like.

Tape Backing

A particular contemplated use for the nonwoven web is as a tape backing capable of being firmly bonded to skin and removed therefrom (e.g., by peeling or stretching at an angle less than about 35 degrees). The highly extensible backing (having a Young's modulus of less than 345 MPa and preferably between 34.5 and 207 MPa) deforms along a propagation front creating a concentration of stress at the propagation front. The tape can thus be removed cleanly at low forces yet provide a strong bond in use. The adhesive for this application should generally be extensible, yet can otherwise be of conventional formulations such as tackified natural or synthetic rubber pressure sensitive adhesives or acrylic based adhesives. When applied, the tape should be unstretched or stretched to a low extent (e.g., to enhance conformability) so that the backing is still highly extensible (e.g., elongation greater than 50%, and preferably greater than 150%).

Heat Bonding to a Substrate (e.g., an ostomy appliance)

The webs of the present invention all comprise a sufficient amount of a material capable of heat or sonic bonding to itself or other materials (e.g., the heat bondable layer material, the heat bondable microfiber, or the heat bondable staple fiber) to enable the resultant elastomeric web to be heat bonded to a structure such as a plastic film. In the first embodiment the combination of an elastomeric layer (as a core layer or the like) and an outer bonding layer provides elastomeric webs capable of heat or sonic bonding to structures such as polyethylene polymer or copolymer films or webs (such as EVA). This finds particular use where properties of conformability, elasticity and breathability are important, and where the web could be heat or sonically bonded to other components of a device, such as medical devices or incontinent devices (e.g., an ostomy bag or the like). Likewise both the second and third embodiments comprise a sufficient quantity of bonding material to enable the resulting web to be heat bonded to a device. Preferred webs comprise at least 10 percent heat bondable material, more preferably 20 percent heat bondable material, and most preferably at least 30 percent heat bondable material. Preferred webs for use in an ostomy appliance have a T-peel strength of at least about 1 N/cm, more preferably at least about 2 N/cm, most preferably at least 2.5 N/cm when bonded to the ostomy appliance film. Most preferably the peel strength mode of failure is either web delamination or web breakage (as opposed to a complete or clean separation mode).

Adhesive Layer

The nonwoven web can be coated with any conventional hot melt, solvent coated, or like adhesive suitable for application to nonwoven webs. These adhesives can be applied by conventional techniques, such as solvent coating by methods such as reverse roll, knife-over-roll, gravure, wire wound rod, floating knife or air knife, hot-melt coating such as by slot orifice coaters, roll coaters or extrusion coaters, at appropriate coating weights. U.S. Pat. No. 5,230,701 (Meyer et al.), which is herein incorporated by reference, discloses suitable adhesive coating methods. In a presently preferred method, the adhesive is first coated on a liner material, using one of the aforementioned techniques, and then laminated (e.g., using a roller to apply pressure) to the nonwoven web. This transfer coating operation avoids saturation of the web with adhesive. More preferably, the fibers may be directly blown against an adhesive.

The extensible nature of the web can have considerable effects on a previously applied adhesive layer. When the web is stretched, the adhesive layer, if continuous, will break up resulting in a porous tape. Adhesives can also be applied after the web has been extended or stretched. Preferred for most applications would be pressure sensitive adhesives. Suitable pressure sensitive adhesives for use in the present invention include those pressure sensitive adhesives which are capable of providing the necessary amount of peel strength and/or shear strength to function in the manner required (e.g., sufficient strength to securely attach the ostomy appliance to the skin without unintended detachment). Suitable adhesives for use in the medical field should be non-toxic, preferably hypoallergenic, and are most preferably also environmentally safe.

Suitable pressure sensitive acrylate adhesives for use in the present invention include copolymers which are reaction products of the polymerization of at least one "A" monomer and at least one "B" monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available. The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices. The commercially available medical tapes described herein using acrylate pressure sensitive adhesives of the type described herein are generally considered hypoallergenic. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. If desired, acrylate pressure sensitive adhesives have a tackifier added to the formulation to improve tack. Commercially available tackifiers include "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention are hypoallergenic Kraton rubber-based pressure sensitive adhesives produced using styrene-butadiene or styrene-isoprene copolymers commercially available as Kraton branded copolymers from Shell Oil Company of Houston, Tex. A variety of Kraton based pressure sensitive adhesives are disclosed in U.S. Pat. Nos. 5,019,071 (Bany et al.) and 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez TM 1310LC branded tackifier commercially available from Exxon Chemicals, a solid $C_5$ tackifying resin commercially available as Wingtack TM Plus brand tackifier from Goodyear Tire and Rubber Company, Akron, Ohio and naphthenic oils having 10% aromatics commercially available as Shellflex TM 371 from Shell Oil Company. Such tackifiers can comprise about 45 to about 70 weight percent of the pressure sensitive adhesive, while the Kraton copolymer can comprise about 30 to 55 weight percent.

Additional alternate pressure sensitive adhesives useful in the present invention are the water-dispersible pressure sensitive adhesives disclosed in U.S. Pat. Nos. 3,865,770; 4,413,080; 4,569,960; 5,125,995; and 5,270,111 and in U.S. patent application Ser. Nos. 07/763,823; 07/889,647; and 8/093,080 the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry,* Saunders et al. (Halsted Publishing Company, New York 1973); *Applied Polymer Science,* Tess et al. (American Chemical Society, Washington, D.C., 1981); *Principles of Polymerization,* Odien (John Wiley and Sons, New York, 1981); and the *Handbook Of Pressure-Sensitive Adhesive Technology, Second Edition,* Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/U.S. Pat. No. Re. 24,906 (Ulrich), the disclosure of which is incorporated by reference herein.

Figure 7A:
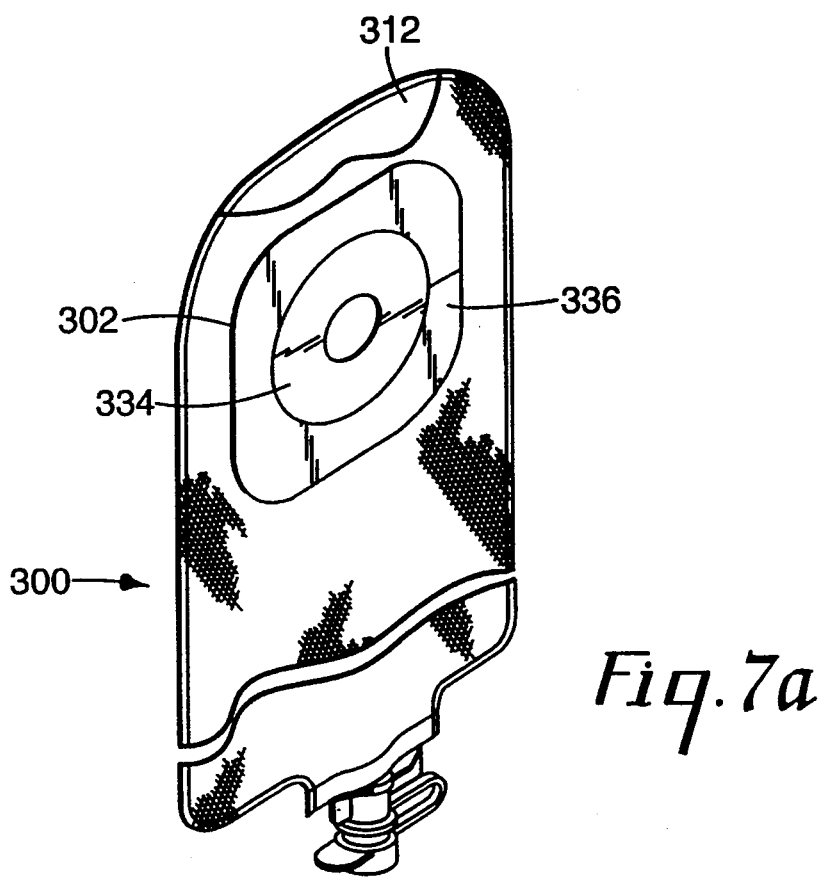
FIGS. 7a and 7b are perspective views of an ostomy bag of the present invention.

FIG. 7a illustrates an ostomy appliance 300 incorporating an attachment means comprising a web of elastomeric medical tape of the present invention. The ostomy bag 312 is provided with a hole 314 surrounded by an attachment means 302 for connecting the bag to a person's skin. The bag side of the attachment means 302 is preferably secured to the bag using a heat or sonic bonding technique. The skin side of the attachment means is coated with a pressure sensitive adhesive and covered prior to use with a liner material 330. If desired, the liner material may optionally be provided in two or more pieces, thus facilitating removal (e.g., by peeling) and/or also facilitating application to the skin (e.g., wherein a portion of the liner material 334 is first removed to expose adhesive and a second portion of the liner 336 functions as a stiffening ring which is removed after the exposed portion of the attachment means is pressed against the skin).

Figure 7B:
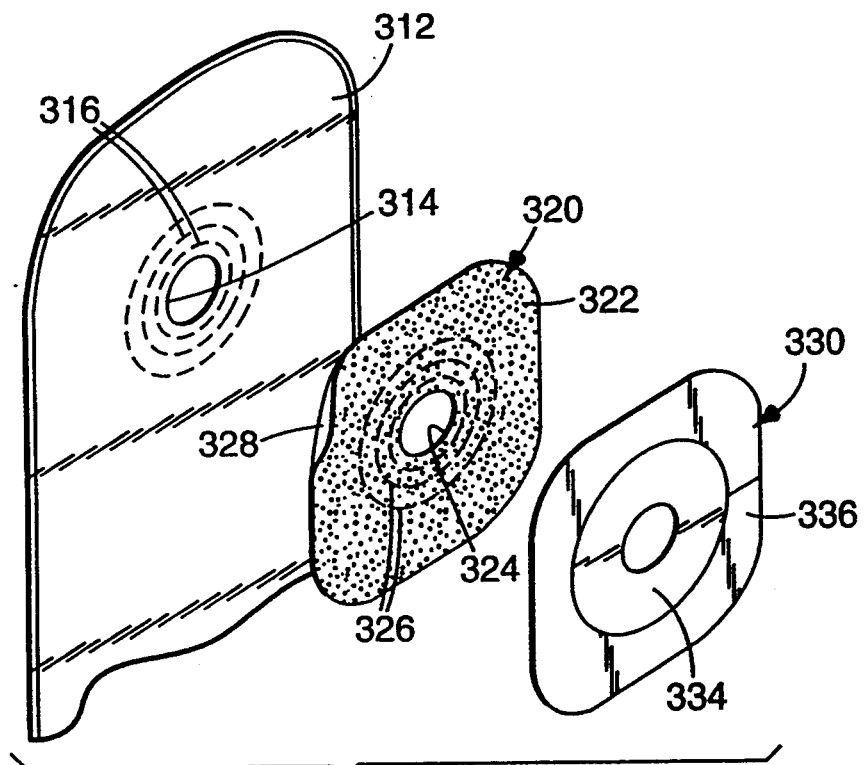

FIG. 7b further illustrates the construction of the ostomy appliance 300. Bag 312 (top portion shown) is provided with an opening 314. A piece of elastomeric medical tape 320 is heat bonded (shown as 316 and 326) to the bag around the opening. The tape has an opening 324 which is positioned in-line with the opening of the bag. A portion of the tape piece 328 is not bonded to the bag. The skin side of the tape piece is coated with adhesive 322. Prior to use the adhesive is protected with a liner 330.

If desired, the attachment means and ostomy bag may be constructed as two separable parts which are connected or disconnected by the user as desired (not shown). For example, the elastomeric medical tape may be heat or sonically bonded to a plastic snap ring. The snap ring mates with a second complimentary snap ring which is heat or sonically bonded to the bag. In this manner the user may remove the bag from the stoma without peeling off the attachment means from the skin. When assembled the snap ring provides a tight leak free seal.

The following examples are provided to illustrate presently contemplated preferred embodiments and the best mode for practicing the invention, but are not intended to be limiting thereof.

TEST PROCEDURES

Tensile Modulus

Tensile modulus data on the multilayer BMF webs was obtained using an Instron Tensile Tester (Model 1122) with a 10.48 cm (2 in.) jaw gap and a crosshead speed of 25.4 cm/min. (10 in./min.). Web samples were 2.54 cm (1 in.) in width. Elastic recovery behavior of the webs was determined by stretching the sample to a predetermined elongation and measuring the length of the sample after release of the elongation force and allowing the sample to relax for a period of 1 minute.

Wide Angle X-Ray Scattering Test

X-Ray diffraction data were collected using a Philips APD-3600 diffractometer (fitted with a Paur HTK temperature controller and hot stage). Copper K $\delta$ radiation was employed with power tube settings of 45 kV and 4 mA and with intensity measurements made by means of a Scintillation detector. Scans within the 2-50 degree ($2\theta$) scattering region were performed for each sample at 25 degrees C. and a 0.02 degree step increment and 2 second counting time.

Conformability

Conformability was measured according to the manufacturer's directions on a Handle-o-Meter ™ Model 211, available from Thwing-Albert Instrument Co. using an 8 in.×8 in. (20.3 cm×20.3 cm) sample using a ¼ in. (0.64 cm) slot width.

Thermal Properties

Melting and crystallization behavior of the polymeric components in the multilayered BMF webs were studied using a Perkin-Elmer Model DSC-7 Differential Scanning Calorimeter equipped with a System 4 analyzer. Heating scans were carried out at 10° or 20° C. per minute with a holding time of three (3) minutes above the melting temperature followed by cooling at a rate of 10° C. per minute. Areas under the melting endotherm and the crystallization exotherm provided an indication of the amount of crystallinity in the polymeric components of the multilayered BMF webs.

Basis Weight

A 10×10 centimeter (cm) sample was cut from the elastic nonwoven web and weighed to the nearest ±0.001 gram. The weight was multiplied by 100 and reported as basis weight in grams/meter$^2$.

Tensile Strength, Percent Elongation, and Force Value at 5, 10, and 25 Percent Elongation Tensile strength, percent elongation and force value (Fn) at 5, 10, and 25 Percent elongation of the elastic nonwoven web tapes were measured using an Instron Tensile Tester (Model 1122) from Instron Corporation, Canton, Mass., with a 2.54 cm gauge length, a crosshead speed of 25.4 cm/min and a chart speed of 25.4 cm/min. The test procedure is based on PSTC-31, ASTM D882 and D3759 Test Methods. The tape samples were razor cut with the length (approximately 12.7 cm) in the machine direction and 2.54 cm in width. The single adhesive coated tapes were folded over at each end of the sample, adhesive to adhesive, to form 2.54 cm tabs to insert in the jaws leaving only the specified gauge length exposed.

Tensile strength is the maximum force applied to the tape sample to obtain the tensile value at point of rupture or break. The tensile strength was reported in newtons/centimeter (N/cm).

Elongation is the maximum percent of stretch reached by the tape sample at the point of rupture or break.

Force Value (Fn) is the force (F) required to elongate the tape sample a specified percent (n). (n) was 5, 10, and 25 percent for the examples. F5, F10, and F25 were reported in newtons/centimeter.

Moisture Vapor Transmission Rate (MVTR)

Moisture Vapor Transmission Rate test method is based on ASTM E96-80 Water Method. The tapes to be sampled were conditioned at 22.8° C.±2° C. (73° F.±3.5° F.) and at 50±5 percent relative humidity for 24 hours. A 4 ounce glass jar with a 3.81 cm diameter hole centered in a screw-on cap was filled with 50 ml of water. Three 35 mm diameter samples were die cut from each type of tape. The sample was centered over the adhesive side of a 5.07 cm$^2$ area hole of a toil adhesive ring. The sample and foil ring hole were lined up with a second foil ring with a 5.07 cm$^2$ area hole forming a foil/sample/foil assembly that was flat, wrinklefree and that had no void areas in the sample area. A 4.445 cm diameter rubber washer was placed on the jar lip. The foil/sample/foil assembly was placed on the rubber washer with the adhesive side of the tape sample down. The screw on cap was placed loosely on the jar. The jars complete with assemblies were placed in a constant temperature and relative humidity chamber for four hours at 38° C.±0.6° C. (100° F.±1° F.) and 10±2 percent relative humidity. The screw on cap was tightened so that sample material was level with the cap and the rubber washer was seated. The jars were removed from the chamber after four hours and weighed to the nearest 0.01 gram ($W_1$=initial weight). The jars were returned to the chamber for at least 18 hours. After at least 18 hours the jars were removed from the chamber and weighed again ($W_2$=final weight). The moisture vapor transmission in grams/meter$^2$ in 24 hours was calculated for each sample using the following:

$$MVTR = \frac{(W_1 - W_2)4.74 \times 10^4}{T(\text{hours})}$$

The three readings for each type tape were averaged and reported to the nearest gram.

Elastic Recovery

Elastic recovery of the elastic nonwoven web tapes was measured using an Instron Tensile Tester (Model 1122) from Instron Company, Corporation, Canton, Mass., with a 2.54 cm gauge length, a crosshead speed of 12.7 cm/min and a chart speed of 12.7 cm/min. One sample was cut 2.54 cm in width and approximately 10.16 cm in length in the machine direction (MD) and another sample was cut the same size in the cross machine direction (CD). The samples were placed in the jaws of the Instron Tensile Tester and stretched to 25 percent elongation. After a dwell period of 5 seconds, the sample was allowed to return to its original length. Elastic recovery was measured as the percentage of the original elongation at the point the force returns to zero, i.e. recovery=(1−stress at the point strain returns to 0)/(original stress). It represents the amount of recoverable energy; the remaining energy is used to deform the web. The greater the percent recovery, the more elastic the material, and the better suited the tape is for skin applications.

. Heat Seal Strength

Heat seals were measured by using a Sentinel Sealer (Model No. 12-AS from Sentinel Heat Sealer, Hyannis, Mass.) at a pressure of 0.2758 MPa, a dwell time of 1 second and at various temperatures shown in Table 19. The elastic web was sealed to the surface of 15/85 ethylene vinyl acetate copolymer film (Cryovac MF 375 from Grace GmbH, D2000 Norderstadt, Germany) which is commonly used in the manufacture of ostomy pouches. This film is a three layer construction, having an EVA film layer at each surface and a PVDC center. After sealing the sample assemblies were peeled apart using a modified "T"-Peel Adhesion Test.

"T"-Peel Adhesion of the heat seals between the elastic nonwoven web tapes and the copolymer film was measured using an Instron Tensile Tester (Model 1122) from Instron Corporation, with a 2.54 cm gauge length and a crosshead speed of 30.48 cm/min. The scope of this test was to measure the peel force for a 2.54 cm wide heat seal between the tape and the film as the seal was pulled apart at a constant rate at 180° peel angle. A sample was cut from the sealed assembly approximately 2.54 cm in width and 15.24 cm in length using a specimen cutter in the machine direction of the tape. Each end of the samples were squarely tabbed crosswise with a 2.54 cm wide piece of tabbing tape and overlapped once in such a way as to leave only the specified gauge length exposed. The test sample assembly was separated at the tabbed ends to insert into the Instron Tensile Tester. The tape end of the sample was clamped to the lower jaw and the film end to the upper jaw. The peel strength of the 2.54 cm width of heat seal was recorded in newtons/cm.

The mode of failure was also rated subjectively as "c"=complete separation i.e., peelable; "wd"=web delamination; and "w"=web broke. A wd or w means a good seal. However, if the peel force is high enough, the seal is acceptable regardless of the mode of failure.

EXAMPLE 1

A polypropylene/polyurethane multilayer BMF web of the present invention was prepared using a melt-blowing process similar to that described, for example, in Wente, Van A., "Superfine Thermoplastic Fibers," in *Industrial Engineering Chemistry*, Vol. 48, pages 1342 et seq (1956), or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized two extruders, each of which was equipped with a gear pump to control the polymer melt flow, each pump feeding a five-layer feedblock splitter assembly similar to that described in U.S. Pat. Nos. 3,480,502 (Chisholm et al.) and 3,487,505 (Schrenk) which was connected to a melt-blowing die having circular smooth surfaced orifices (10/cm) with a 5:1 length to diameter ratio. The first extruder (260° C.) delivered a melt stream of a 800 melt flow rate (MFR) polypropylene (PP) resin (PP 3495G, available from Exxon Chemical Corp.), to the feedblock assembly which was heated to about 260° C. The second extruder, which was maintained at about 220° C., delivered a melt stream of a poly(esterurethane) (PU) resin ("Morthane TM" PS 455-200, available from Morton International, Inc.) to the feedblock. The feedblock split the two melt streams. The polymer melt streams were merged in an alternating fashion into a five-layer melt stream on exiting the feedblock, with the outer layers being the PP resin.

The gear pumps were adjusted so that a 75:25 pump ratio percent (i.e., volume percent) PP:PU polymer melt was delivered to the feedblock assembly and a 0.14 kg/hr/cm die width (0.8 lb/hr/in.) polymer throughput rate was maintained at the BMF die (260° C.). The primary air temperature was maintained at approximately 220° C. and at a pressure suitable to produce a uniform web with a 0.076 cm gap width. Webs were collected at a collector to BMF die distance of 30.5 cm (12 in.). The resulting BMF web, comprising five-layer microfibers having an average diameter of less than about 10 micrometers, had a basis weight of 50 g/m$^2$.

EXAMPLE 2

A BMF web having a basis weight of 50 g/m$^2$ and comprising five-layer microfibers having an average diameter of less than about 10 micrometers was prepared according to the procedure of Example 1, except that the PP and PU melt streams were delivered to the five-layer feedblock in a 50:50 ratio.

EXAMPLE 3

A BMF web having a basis weight of 50 g/m² and comprising five-layer microfibers having an average diameter of less than about 10 micrometers was prepared according to the procedure of Example 1, except that the PP and PU melt streams were delivered to the five-layer feedblock in a 25:75 ratio.

CONTROL WEB I

A control web of the 800 MFR polypropylene resin was prepared according to the procedure of Example 1, except that only one extruder, which was maintained at 260° C., was used, and it was connected directly to the BMF die through a gear pump. The die and air temperatures were maintained at 260° C. The resulting BMF web had a basis weight of 50 g/m² and an average fiber diameter of less than about 10 micrometers.

CONTROL WEB II

A control web of the polyurethane resin ("Morthane ™" PS455-200) was prepared according to the procedure of Example 1, except that only one extruder, which was maintained at 220° C., was used which was connected directly to the BMF die through a gear pump. The die and air temperatures were maintained at 220° C. The resulting BMF web had a basis weight of 50 g/m² and an average fiber diameter of less than about 10 micrometers.

Table 1 summarizes the tensile modulus values for BMF webs comprising five-layer microfibers of varying PP/PU polymer ratios.

TABLE 1

Tensile Modulus
Five-layer PP/PU BMF Webs
50 g/m² Basis Weight

| | | Tensile Modulus | |
|---|---|---|---|
| Example | Pump Ratio PP/PU | MD kPa | XMD kPa |
| Control I | 100:0 | 2041 | 2897 |
| 1 | 75:25 | 6821 | 9235 |
| 2 | 50:50 | 8083 | 9490 |
| 3 | 25:75 | 8552 | 12214 |
| Control II | 0:100 | 1055 | 1814 |

EXAMPLE 4

Figure 6:
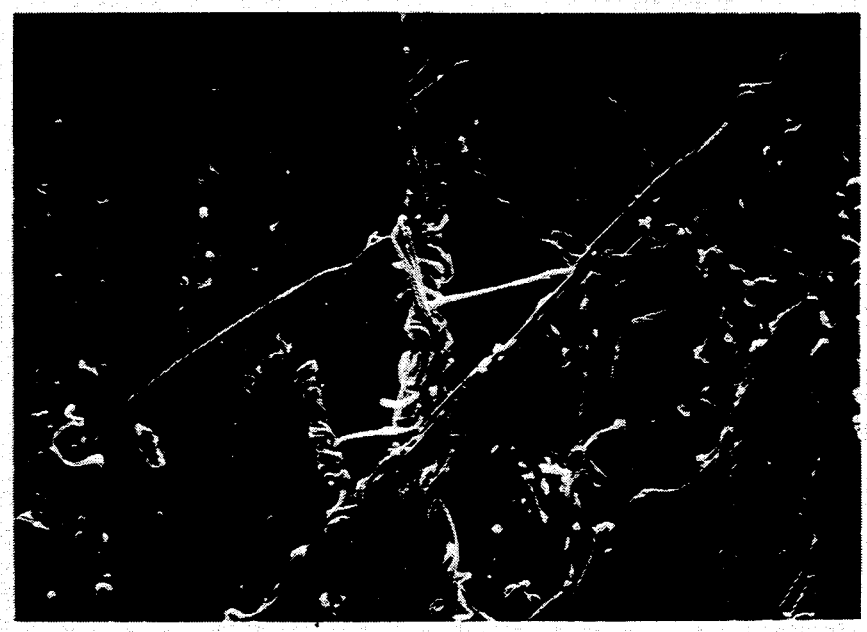
FIG. 6 is a scanning electron micrograph top view of an Example 4 web.

A BMF web having a basis weight of 100 g/m² and comprising two-layer microfibers having an average diameter of less than about 10 micrometers was prepared according to the procedure of Example 3, except that the PP and PU melt streams were delivered to a two-layer feedblock, and the die and air temperatures were maintained at about 230° C. This sample was stretched 200% and released. This sample was then prepared for scanning electron micrograph analysis. FIG. 6 shows a top view of this stretched sample (200×). The machine direction conformability was 174 grams, and the cross direction conformability was 227 grams.

EXAMPLE 5

A BMF web having a basis weight of 100 g/m² and comprising three-layer microfibers having an average diameter of less than about 10 micrometers was prepared according to the procedure of Example 3, except that the PP and PU melt streams were delivered to a three-layer feedblock. The machine direction conformability was 188 grams, and the cross direction conformability was 277 grams.

EXAMPLE 6

A BMF web having a basis weight of 100 g/m² and comprising five-layer microfibers having an average diameter of less than about 10 micrometers was prepared according to the procedure of Example 3. Example 3 is a five-layer construction. The machine direction conformability was 185 grams, and the cross direction conformability was 252 grams.

EXAMPLE 7

A BMF web having a basis weight of 100 g/m² and comprising twenty-seven-layer microfibers having an average diameter of less than about 10 micrometers was prepared according to the procedure of Example 3, except that the PP and PU melt streams were delivered to a twenty-seven-layer feedblock. The machine direction conformability was 149 grams, and the cross direction conformability was 185 grams.

Table 2 summarizes the modulus values for a series of BMF webs having a 25:75 PP:PU pump ratio, but varying numbers of layers in the microfibers.

TABLE 2

Web Modulus as a Function of Layers in Microfiber
25:75 PP/PU Pump Ratio
100 g/m² Basis Weight

| Example | Number of Layers | MD Tensile Modulus (kPa) |
|---|---|---|
| 4 | 2 | 10835 |
| 5 | 3 | 11048 |
| 6 | 5 | 15014 |
| 7 | 27 | 17097 |

Figure 2:
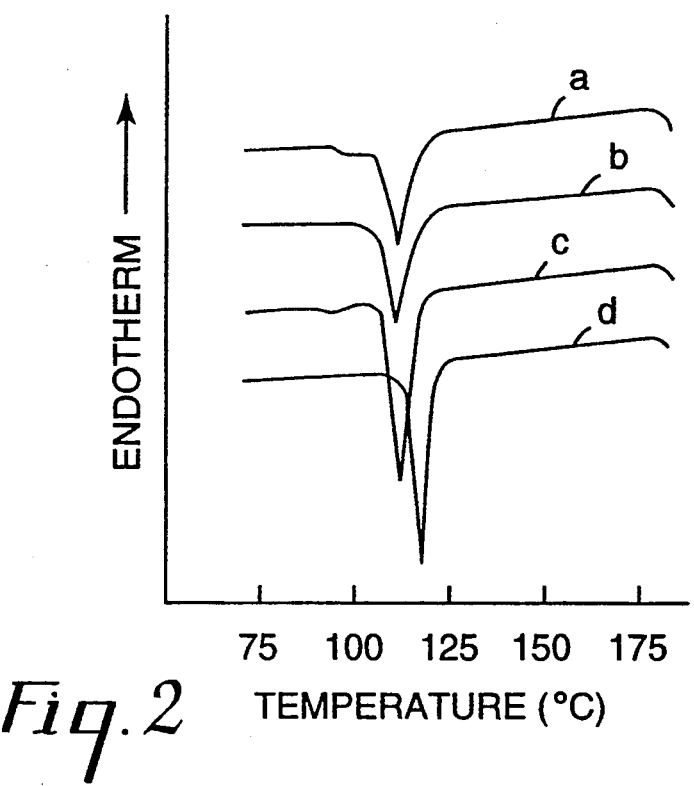
FIG. 2 is a plot of differential scanning calorimetry scans or Examples 4–7 showing increasing exotherms with increasing layering.
Figure 3:
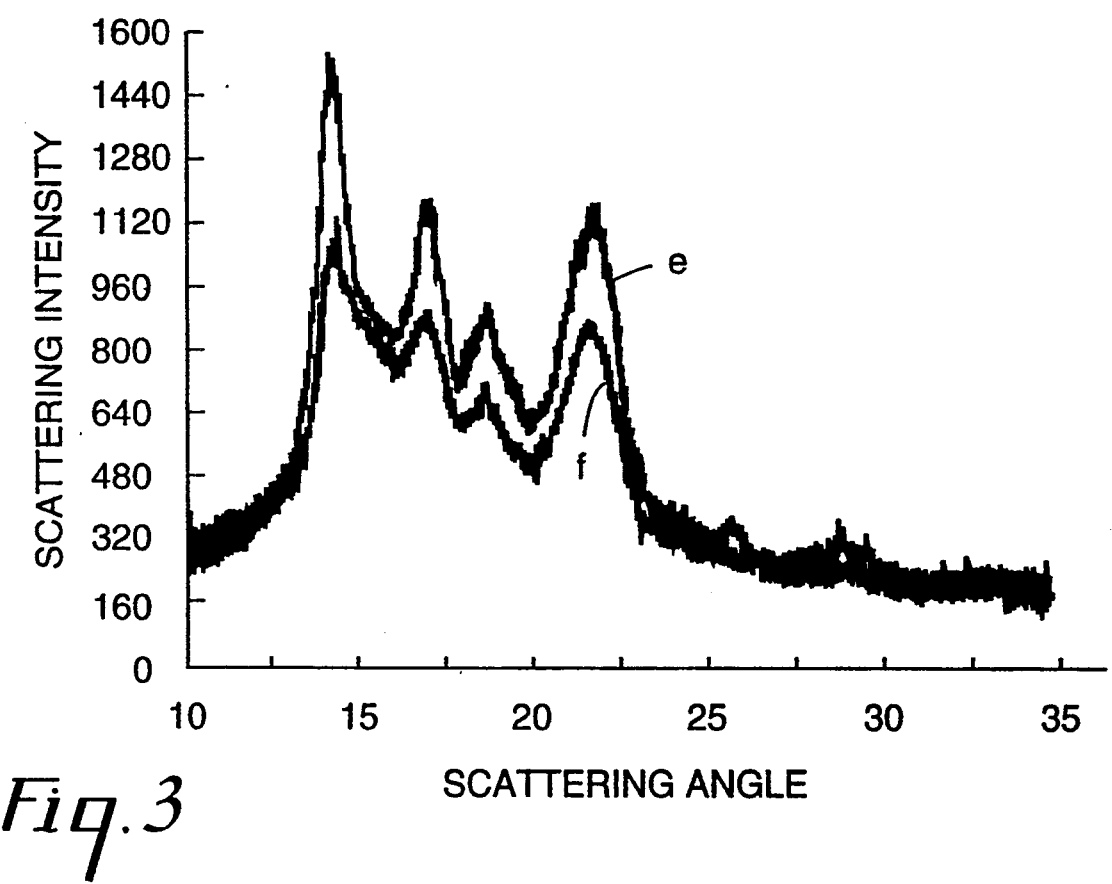
FIG. 3 is a plot of wide-angle x-ray scattering for Examples 5 and 7 showing increasing crystallinity with increasing layering.

The effect that the number of layers within the microfiber cross-section had on the crystallization behavior of the PP/PU BMF webs was studied using differential scanning calorimetry the results of which are graphically presented in FIG. 2. An examination of the crystallization exotherms for the BMF webs of Examples 4, 5, 6 and 7 (a, b, c and d, respectively), which corresponds to blown microfibers having 2, 3, 5 and 27 layers, respectively, indicates that the peak of the crystallization exotherm for the web of Example 7 is approximately 6° C. higher than the corresponding peak values for webs comprising blown microfibers having fewer layers. This data suggests that the crystallization process is enhanced in the microfibers having 27 layers, which is further supported by the examination of the wide angle X-ray scattering data that is illustrated in FIG. 3 and confirms higher crystallinity in the PP of the 27 layer microfiber web samples (e corresponds to Example 7 and f corresponds to Example 5 after washing out the PU with tetrahydrofuran solvent).

EXAMPLE 8

A BMF web having a basis weight of 100 g/m² and comprising two-layer microfibers having an average diameter of less than about 10 micrometers was prepared according to the procedure of Example 1, except that a 105 MI low-density polyethylene (LLDPE, Aspun ™ 6806 available from Dow Chemical) was substituted for the polypropylene and a poly(esterurethane) (PU) resin ("Morthane ™" PS 440-200, available from Morton International, Inc.) was substituted for the Morthane ™ PS 455-200, the extruder temperatures were maintained at 220° C. and 230° C., respectively, the melt streams were delivered to a two-layer feedblock maintained at 230° C. at a 75:25 ratio, the BMF die and primary air supply temperatures were maintained at 225° C. and 215° C., respectively, and the collector distance was 30.5 cm. The machine direction conformability was 157 grams, and the cross direction conformability was 181 grams.

EXAMPLE 9

A BMF web having a basis weight of 100 g/m² and comprising two-layer microfibers having an average diameter of less than about 10 micrometers was prepared according to the procedure of Example 8, except that the PE and PU melt streams were delivered to the two-layer feedblock in a 50:50 ratio. The machine direction conformability was 115 grams, and the cross direction conformability was 150 grams.

EXAMPLE 10

A BMF web having a basis weight of 100 g/m² and comprising two-layer microfibers having an average diameter of less than about 10 micrometers was prepared according to the procedure of Example 8, except that the PE and PU melt streams were delivered to the two-layer feedblock in a 25:75 ratio. The machine direction conformability was 70 grams, and the cross direction conformability was 103 grams.

CONTROL WEB III

A control web of the LLDPE resin (Aspun ™ 6806) was prepared according to the procedure of Example 1, except that only one extruder, which was maintained at 210° C., was used, and it was connected directly to the BMF die through a gear pump, and the die and air temperatures were maintained at 210° C., and the collector distance was 25.4 cm. The resulting BMF web had a basis weight of 100 g/m² and an average fiber diameter of less than about 10 micrometers.

CONTROL WEB IV

A control web of the polyurethane resin (Morthane ™ PS440-200) was prepared according to the procedure of Example 1, except that only one extruder, which was maintained at 230° C., was used which was connected directly to the BMF die through a gear pump, and the die and air temperatures were maintained at 230° C. The resulting BMF web had a basis weight of 100 g/m² and an average fiber diameter of less than about 10 micrometers.

Table 3 summarizes the tensile modulus values for BMF webs comprising two-layer microfibers of varying PE/PU compositions.

TABLE 3

Tensile Modulus
Two-Layer PE/PU BMF Webs
100 g/m² Basis Weight

| Example | Pump Ratio (parts PE/PU) | MD Tensile Modulus (kPa) |
|---|---|---|
| Control III | 100:0 | 1172 |
| 8 | 75:25 | 4923 |
| 9 | 50:50 | 3737 |
| 10 | 25:75 | 2654 |
| Control IV | 0:100 | 2130 |

EXAMPLE 11

A BMF web having a basis weight of 50 g/m² and comprising five-layer microfibers having an average diameter of less than about 10 micrometers was prepared according to the procedure of Example 1, except that a poly(ethylene terephthalate) resin (PET having an I.V.=0.60 and a melting point of about 257° C., prepared as described in U.S. Pat. No. 4,939,008, col. 2, line 6 to col. 3, line 20) was substituted for the polypropylene and a poly(esterurethane) (PU) resin (Morthane ™ PS 440-200, available from Morton International, Inc.) was substituted for the Morthane ™ PS 455-200 (in a 75:25 ratio), the melt streams were delivered to the five-layer feedblock at about 280° C. and about 230° C., respectively, and the feedblock, die and air temperatures were maintained at 280° C., 280° C. and 270° C., respectively.

EXAMPLE 12

A BMF web having a basis weight of 50 g/m² and comprising five-layer microfibers having an average diameter of less than about 10 micrometers was prepared according to the procedure of Example 11, except that the PET and PU melt streams were delivered to the five-layer feedblock in a 50:50 ratio.

EXAMPLE 13

A BMF web having a basis weight of 50 g/m² and comprising five-layer microfibers having an average diameter of less than about 10 micrometers was prepared according to the procedure of Example 11, except that the PET and PU melt streams were delivered to the five-layer feedblock in a 25:75 ratio.

CONTROL WEB V

A control web of the poly(ethylene terephthalate) (I.V.=0.60) resin was prepared according to the procedure of Example 1, except that only one extruder, which was maintained at about 300° C., was used which was connected directly to the BMF die through a gear pump, and the die and air temperatures were maintained at 300° C. and 305° C., respectively. The resulting BMF web had a basis weight of 100 g/m² and an average fiber diameter of less than about 10 micrometers.

Table 4 summarizes the tensile modulus values for BMF webs comprising five-layer microfibers of varying PET/PU ratios.

TABLE 4

Tensile Modulus
Five-Layer PET/PU BMF Webs
50 g/m² Basis Weight

| Example | Pump Ratio (parts PET/PU) | MD Tensile Modulus (kPa) |
|---|---|---|
| Control V | 100:0 | 772[1] |
| 11 | 75:25 | 9674 |
| 12 | 50:50 | 10770 |
| 13 | 25:75 | 12376 |
| Control VI | 0:100 | 1834 |

[1]100 g/m² basis weight.

Example 14

A BMF web having a basis weight of 50 g/m² and comprising five-layer microfibers having an average diameter of less than about 10 micrometers was prepared according to the procedure of Example 1, except that a 60/40 blend of Kraton™ G-1657, a hydrogenated styrene/ethylenebutylene/styrene A-B-A block copolymer (SEBS) available from Shell Chemical Corp., and a linear low-density polyethylene (LLDPE) Aspun™ 6806, 105 MI, available from Dow Chemical, was substituted for the Morthane™ PS 455-200, the extruder temperatures were maintained at 250° C. and 270° C., respectively, the melt streams were delivered to a five-layer feedblock maintained at 270° C. at a 75:25 ratio, and the die and primary air temperatures were maintained at 270° C. and 255° C., respectively.

Example 15

A BMF web having a basis weight of 50 g/m² and comprising five-layer microfibers having an average diameter of less than about 10 micrometers was prepared according to the procedure of Example 14, except that the PP and SEBS/LLDPE blend melt streams were delivered to the five-layer feedblock in a 50:50 ratio.

Example 16

A BMF web having a basis weight of 50 g/m² and comprising five-layer microfibers having an average diameter of less than about 10 micrometers was prepared according to the procedure of Example 14, except that the PP and SEBS/LLDPE blend melt streams were delivered to the five-layer feedblock in a 25:75 ratio.

CONTROL WEB VI

A control web of the 60/40 SEBS/LLDPE blend was prepared according to the procedure of Example 1, except that only one extruder, which was maintained at 270° C., was used which was connected directly to the BMF die through a gear pump, and the die and air temperatures were maintained at 270° C. The resulting BMF web had a basis weight of 50 g/m² and an average fiber diameter of less than about 10 micrometers.

Table 5 summarizes the tensile modulus values for BMF webs comprising five-layer microfibers of varying PP//SEBS/LLDPE ratios.

TABLE 5

Tensile Modulus
Five-Layer PP//SEBS/LLDPE BMF Webs
50 g/m² Basis Weight

| Example | Pump Ratio (parts PP/Blend) | MD Tensile Modulus (kPa) |
|---|---|---|
| Control I | 100:0 | 2034 |
| 14 | 75:25 | 18685 |
| 15 | 50:50 | 12011 |
| 16 | 25:75 | 6978 |
| Control VI | 0:100 | 434 |

Example 17

A BMF web having a basis weight of 50 g/m² and comprising two-layer microfibers having an average diameter of less than about 10 micrometers was prepared according to the procedure of Example 14, except that a two-layer feedblock assembly was substituted for the five-layer feedblock.

Example 18

A BMF web having a basis weight of 50 g/m² and comprising two-layer microfibers having an average diameter of less than about 10 micrometers was prepared according to the procedure of Example 17, except that the PP and SEBS/LLDPE blend melt streams were delivered to the two-layer feedblock in a 50:50 ratio.

Example 19

A BMF web having a basis weight of 50 g/m² and comprising two-layer microfibers having an average diameter of less than about 10 micrometers was prepared according to the procedure of Example 17, except that the PP and SEBS/LLDPE blend melt streams were delivered to the two-layer feedblock in a 25:75 ratio.

Table 6 summarizes the tensile modulus values for BMF webs comprising two-layer microfibers of varying PP//SEBS/LLDPE compositions.

TABLE 6

Tensile Modulus
Two-Layer PP//SEBS/LLDPE BMF Webs
50 g/m² Basis Weight

| Example | Pump Ratio PP/Blend | MD Tensile Modulus kPa |
|---|---|---|
| Control I | 100:0 | 2034 |
| 17 | 75:25 | 10197 |
| 18 | 50:50 | 7357 |
| 19 | 25:75 | 3103 |
| Control VI | 0:100 | 434 |

Example 20

A BMF web having a basis weight of 100 g/m² and comprising two-layer microfibers having an average diameter of less than about 10 micrometers was prepared according to the procedure of Example 8, except that the collector distance was 15.2 cm (6 in.).

Example 21

A BMF web having a basis weight of 100 g/m² and comprising two-layer microfibers having an average diameter of less than about 10 micrometers was prepared according to the procedure of Example 9, except that the collector distance was 15.2 cm (6 in.). The machine direction conformability was 101 grams, and the cross direction conformability was 162 grams.

Example 22

A BMF web having a basis weight of 100 g/m² and comprising two-layer microfibers having an average diameter of less than about 10 micrometers was prepared according to the procedure of Example 10, except that the collector distance was 15.2 cm (6 in.). The machine direction conformability was 56 grams, and the cross direction conformability was 85 grams.

Table 7 summarizes the MD modulus values for a number of two-layer PE/PU web compositions which were prepared utilizing two collector distances.

TABLE 7

Web Modulus as a Function of Collector Distance
for Various Two-Layer PE/PU Pump Ratios
100 g/m² Basis Weight

| Example | Pump Ratio PE/PU | Collector Distance (cm) | MD Tensile Modulus (kPa) |
|---|---|---|---|
| 8 | 75:25 | 30.5 | 4923 |
| 20 | 75:25 | 15.2 | 12590 |
| 9 | 50:50 | 30.5 | 3737 |
| 21 | 50:50 | 15.2 | 9494 |
| 10 | 25:75 | 30.5 | 2654 |

TABLE 7-continued

Web Modulus as a Function of Collector Distance
for Various Two-Layer PE/PU Pump Ratios
100 g/m² Basis Weight

| Example | Pump Ratio PE/PU | Collector Distance (cm) | MD Tensile Modulus (kPa) |
|---|---|---|---|
| 22 | 25:75 | 15.2 | 7929 |

Example 23

A BMF web having a basis weight of 100 g/m² and comprising twenty-seven-layer microfibers having an average diameter of less than about 10 micrometers was prepared according to the procedure of Example 7, except that the PP and PU melt streams were delivered to the twenty-seven-layer feedblock such that the outer layer of the fibers was PU rather than PP (I/O vs O/I for Example 7) and the die orifices had a diameter of about 0.0432 cm versus 0.0381 cm for Example 7.

Table 8 summarizes the MD modulus for two twenty-seven-layer layer PP/PU microfiber webs where the order of polymer feed into the feedblock was reversed, thereby inverting the composition of the outer layer of the microfiber.

TABLE 8

Effect of Outside Component
Twenty-Seven-Layer 25/75 PP/PU Pump Ratio
100 g/m² Basis Weight

| Example | Layer Composition | MD Tensile Modulus (kPa) |
|---|---|---|
| 23(a) | O/I | 14390 |
| 23 | I/O | 11632 |

Example 24

A BMF web having a basis weight of 100 g/m² and comprising twenty-seven-layer microfibers having an average diameter of less than about 10 micrometers was prepared according to the procedure of Example 7, except that the PP and PU melt streams were delivered to the twenty-seven-layer feedblock which was maintained at 250° C. in a 75/25 ratio from two extruders which were maintained at 250° C. and 210° C., respectively, and a smooth collector drum was positioned 15.2 cm from the BMF die. The PP and PU melt streams were introduced into the feedblock assembly such that the outer layer of the fiber was PP (O/I).

Example 25

A BMF web having a basis weight of 100 g/m: and comprising twenty-seven-layer microfibers having an average diameter of less than about 10 micrometers was prepared according to the procedure of Example 24, except that the PP and PU melt streams were delivered to the twenty-seven-layer feedblock in a 50/50 ratio. The machine direction conformability was 296 grams, and the cross direction conformability was 507 grams.

Example 26

A BMF web having a basis weight of 100 g/m² and comprising twenty-seven-layer microfibers having an average diameter of less than about 10 micrometers was prepared according to the procedure of Example 24 except that the PP and PU melt streams were delivered to the twenty-seven-layer feedblock in a 25/75 ratio.

Example 27

Figure 4:

A BMF web having a basis weight of 100 g/m² and comprising twenty-seven-layer microfibers having an average diameter of less than about 10 micrometers was prepared according to the procedure of Example 24, except that a LLDPE (Aspun TM 6806, 105 MFR, available from Dow Chemical) was substituted for the PP and the PE and PU melt streams were delivered to the twenty-seven-layer feedblock which was maintained at 210° C. in a 75/25 ratio from two extruders which were both maintained at 210° C. A scanning electron micrograph (FIG. 4—2000×) of a cross section of this sample was prepared after the polyurethane was washed out with tetrahydrofuran. The sample was then cut, mounted and prepared for analysis by standard techniques.

Example 28

A BMF web having a basis weight of 100 g/m² and comprising twenty-seven-layer microfibers having an average diameter of less than about 10 micrometers was prepared according to the procedure of Example 27, except that the PE and PU melt streams were delivered to the twenty-seven-layer feedblock in a 50/50 ratio.

Example 29

A BMF web having a basis weight of 100 g/m² and comprising twenty-seven-layer microfibers having an average diameter of less than about 10 micrometers was prepared according to the procedure of Example 27, except that the PE and PU melt streams were delivered to the twenty-seven-layer feedblock in a 25/75 ratio.

Table 9 summarizes the MD tensile modulus for several twenty-seven-layer microfiber webs where the composition of the outer layer of the fiber varied between PP and PE.

TABLE 9

Effect of PP vs. PE on MD Web Tensile Modulus
27 Layer PP/PU and PE/PU Webs
100 g/m² Basis Weight

| Example | Web Composition Polymers | Ratio | MD Tensile Modulus (kPa) |
|---|---|---|---|
| 24 | PP/PU | 75:25 | 95940 |
| 25 | PP/PU | 50:50 | 46396 |
| 26 | PP/PU | 25:75 | 28090 |
| 27 | PE/PU | 75:25 | 19926 |
| 28 | PE/PU | 50:50 | 12328 |
| 29 | PE/PU | 25:75 | 7819 |

The recovery behavior of BMF webs comprising multilayered BMF fibers was studied by subjecting samples of BMF webs consisting of various multilayered fiber compositions to elongations of 100, 200 and 400% and monitoring the length of the samples after the elongation force had been removed and the samples allowed to relax for a period of one minute. Elastic recovery was calculated using the formula:

$$\% \text{ Elastic Recovery} = \frac{L_{Stretched} - L_{Recovered}}{L_{Stretched} - L_{Initial}} \times 100$$

Results of this study are summarized in Tables 10–15.

Example 30

A BMF web having a basis weight of 100 g/m² and comprising three-layer microfibers having an average diameter of less than about 10 micrometers was prepared according to the procedure of Example 22, except that the PE and PU polymer melt streams were delivered to a three-layer feedblock in a manner such that the outer layer of the fiber was PU (I/O configuration).

Example 31

A BMF web having a basis weight of 100 g/m² and comprising three-layer microfibers having an average diameter of less than about 10 micrometers was prepared according to the procedure of Example 21, except that the PE and PU polymer melt streams were delivered to a three-layer feedblock in a manner such that the outer layer of the fiber was PU (I/O configuration).

Example 32

A BMF web having a basis weight of 50 g/m² and comprising three-layer microfibers having an average diameter of less than about 10 micrometers was prepared according to the procedure of Example 3, except that the PP and PU melt streams were delivered to a three-layer feedblock.

Example 33

A BMF web having a basis weight of 50 g/m² and comprising three-layer microfibers having an average diameter of less than about 10 micrometers was prepared according to the procedure of Example 2 except, that the PP and PU melt streams were delivered to a three-layer feedblock.

Example 34

A BMF web having a basis weight of 75 g/m² and comprising three-layer microfibers having an average diameter of less than about 10 micrometers was prepared according to the procedure of Example 3.

Example 35

A BMF web having a basis weight of 155 g/m² and comprising three-layer microfibers having an average diameter of less than about 10 micrometers was prepared according to the procedure of Example 3.

Example 36

A BMF web having a basis weight of 100 g/m² and comprising three-layer microfibers having an average diameter of less than about 10 micrometers was prepared according to the procedure of Example 3, except that Pellathane TM 2103-80WC, a poly(etherurethane) available from Dow Chemical Corp. was substituted for the Morthane TM PS 455-200, the extruders delivering the PP and PU melts were maintained at 240° C. and 210° C., respectively, the PP and PU melt streams were delivered to a three-layer feedblock, which was maintained at 240° C., and the die and air temperatures were maintained at 230° C. and 215° C., respectively.

Example 37

A BMF web having a basis weight of 190 g/m² and comprising three-layer microfibers having an average diameter of less than about 10 micrometers was prepared according to the procedure of Example 36.

Example 38

A BMF web having a basis weight of 100 g/m² and comprising five-layer microfibers having an average diameter of less than about 10 micrometers was prepared according to the procedure of Example 3, except that Pellathane TM 2103-80WC, a poly(etherurethane) available from Dow Chemical Corp. was substituted for the Morthane TM PS 455-200, the extruders delivering the PP and PU melts were maintained at 240° C. and 210° C., respectively, the PP and PU melt streams were delivered to a five-layer feedblock, which was maintained at 240° C., and the die and air temperatures were maintained at 230° C. and 220° C., respectively.

CONTROL WEB VII

A control web of the poly(etherurethane) resin (Pellathane TM 2103-80WC) was prepared according to the procedure of Example 1, except that only one extruder, which was maintained at 210° C., was used which was connected directly to the BMF die through a gear pump and the die and air temperatures were maintained at 210° C. The resulting BMF web had a basis weight of 100 g/m² and an average fiber diameter of less than about 10 micrometers.

Example 39

A BMF web having a basis weight of 100 g/m² and comprising five-layer microfibers having an average diameter of less than about 10 micrometers was prepared according to the procedure of Example 1, except that Kraton TM G-1657, (SEBS) was substituted for the Morthane TM PS 455-200, both extruder temperatures were maintained at 260° C., the melt streams were delivered to a five-layer feedblock maintained at 240° C. at a 62.5:37.5 ratio, and the die and primary air temperatures maintained at 240° C. and 275° C., respectively.

Example 40

A BMF web having a basis weight of 100 g/m² and comprising five-layer microfibers having an average diameter of less than about 10 micrometers was prepared according to the procedure of Example 39, except that PP and SEBS melt streams were delivered to the feedblock in a 25:75 ratio.

Example 41

A BMF web having a basis weight of 100 g/m² and comprising two layer microfibers having an average diameter of less than about 10 micrometers was prepared according to the procedure of Example 1 except that a poly(esterurethane) (PU) resin (Morthane PS 440-200, available from Morton International, Inc.) was substituted for the Morthane PS 455-200, the second extruder was maintained at 230° C., and the PP and PU melt streams were delivered to the two layer feed block in a 50:50 ratio.

Example 42

A BMF web having a basis weight of 100 g/m² and comprising two layer microfibers having an average diameter of less than about 10 micrometers was prepared according to the procedure of Example 1 except that a poly(esterurethane) (PU) resin (Morthane PS 440-200, available from Morton International, Inc.) was substituted for the Morthane PS 455-200, the second extruder was maintained at 230° C., and the PP and PU melt streams were delivered to the two layer feed block in a 25:75 ratio.

TABLE 10

Recovery Behavior
Multilayered 25:75 PP/PU BMF Webs
100 g/m² Basis Weight

| Ex. | # of Layers | Initial Length (mm) | Post Elongation Length (mm) | Recovered Length (mm) |
|---|---|---|---|---|
| 4 | 2 | 25.4 | 51 | 33.5 |
| 4 | 2 | 25.4 | 76 | 38.8 |
| 4 | 2 | 25.4 | 127 | 48.6 |
| 5 | 3 | 25.4 | 51 | 37.3 |
| 5 | 3 | 25.4 | 76 | 52.5 |
| 5 | 3 | 25.4 | 127 | 86.5 |
| 6 | 5 | 25.4 | 51 | 39.6 |
| 6 | 5 | 25.4 | 76 | 56.8 |
| 6 | 5 | 25.4 | 127 | 95.1 |
| 7 | 27 | 25.4 | 51 | 37.8 |
| 7 | 27 | 25.4 | 76 | 53.5 |
| 7 | 27 | 25.4 | 127 | 92.6 |

TABLE 11

Elastic Recovery
Multilayered 25:75 PP/PU BMF Webs
100 g/m² Basis Weight

| Example | # of Layers | % Recovery After Elongation of 100% | 200% | 400% |
|---|---|---|---|---|
| 4 | 2 | 68 | 74 | 77 |
| 5 | 3 | 54 | 46 | 40 |
| 6 | 5 | 45 | 38 | 31 |
| 7 | 27 | 52 | 45 | 34 |

TABLE 12

Recovery Behavior
Multilayered PE/PU BMF Webs
100 g/m² Basis Weight

| Ex. | Ratio/# of Layers | Initial Length (mm) | Post Elongation Length (mm) | Recovered Length (mm) |
|---|---|---|---|---|
| 22 | (25:75) 2 | 25.4 | 51 | 29.5 |
|  |  | 25.4 | 76 | 34 |
|  |  | 25.4 | 127 | 45 |
| 21 | (50:50) 2 | 25.4 | 51 | 32.3 |
|  |  | 25.4 | 76 | 39.3 |
|  |  | 25.4 | 127 | 47.6 |
| 30 | (25:75) 3 | 25.4 | 51 | 31 |
|  |  | 25.4 | 76 | 39.1 |
|  |  | 25.4 | 127 | 63.3 |
| 31 | (50:50) 3 | 25.4 | 51 | 33 |
|  |  | 25.4 | 76 | 45.3 |
|  |  | 25.4 | 127 | 68.5 |

TABLE 13

Elastic Recovery
Multilayered PE/PU BMF Webs
100 g/m² Basis Weight

| Example | # of Layers | % Recovery After Elongation of 100% | 200% | 400% |
|---|---|---|---|---|
| 22 | 2 | 84 | 83 | 81 |
| 21 | 2 | 73 | 73 | 78 |
| 30 | 3 | 78 | 73 | 63 |
| 31 | 3 | 70 | 61 | 58 |

TABLE 14

Recovery Behavior
PP vs PE Two-Layer BMF
100 g/m² Basis Weight

| Ex. | Poly/Ratio of Layers | Initial Length (mm) | Post Elongation Length (mm) | Recovered Length (mm) |
|---|---|---|---|---|
| 42 | (PP/PU) 25:75 | 25.4 | 51 | 30.9 |
|  |  | 25.4 | 76 | 34.8 |
| 41 | (PP/PU) 50:50 | 25.4 | 51 | 32.3 |
|  |  | 25.4 | 76 | 37.6 |
| 22 | (PE/PU) 25:75 | 25.4 | 51 | 29.0 |
|  |  | 25.4 | 76 | 33.1 |
| 21 | (PE/PU) 50:50 | 25.4 | 51 | 30.8 |
|  |  | 25.4 | 76 | 36.5 |

TABLE 15

Elastic Recovery
PP vs PE in Two-Layer BMF
100 g/m² Basis Weight

| Example | Comp. of Layers | % Recovery After Elongation of 100% | 200% | 400% |
|---|---|---|---|---|
| 42 | PP/PU | 79 | 81 | —* |
| 41 | PP/PU | 73 | 76 | —* |
| 22 | PE/PU | 86 | 85 | —* |
| 21 | PE/PU | 79 | 78 | —* |

*Sample broke on attempting to stretch to 400% elongation.

In addition to monitoring the web recovery under ambient conditions, samples of several webs were subjected to post elongation annealing at elevated temperatures to determine if further recovery would be realized at elevated temperatures. Unless indicated otherwise, the web samples were placed in a circulating air oven at the indicated temperature for a period of 0.5 minutes, and the samples measured to determine if further recovery had occurred. Results of these studies are summarized in Tables 16–18.

TABLE 16

Elastic Recovery Properties of
Polypropylene/Polyurethane (455-200)
Elongated/Annealed Webs

| Example | Comp. Polymer/ Ratio | # Layers | Basis Wt. (g/m2) | Init. Length (mm) | Elong. Length (mm) | Rc'vd. Length (mm) | Sample Orient. | Ann. Temp. (°C.) | PreAnn. Length (mm) | Post Ann. Length (mm) |
|---|---|---|---|---|---|---|---|---|---|---|
| 32 | PP/PU 25/75 | 3 | 50 | 26.9 | 79.7 | 49.3 | XMD | 90 | 43.1[1] | 33.2 |
| 33 | PP/PU 50/50 | 3 | 50 | 26.9 | 79.7 | 53.3 | XMD | 90 | 48.1[1] | 35.2 |
| 3 | PP/PU 25/75 | 5 | 50 | 26.9 | 79.7 | 57.7 | XMD | 90 | 53.4[1] | 43.2 |
| 2 | PP/PU 50/50 | 5 | 50 | 26.9 | 79.7 | 61.2 | XMD | 90 | 56.2[1] | 50.2 |
| 32 | PP/PU 25/75 | 3 | 50 | 26.6 | 53.0 | 36.0 | XMD | 125 | 34.5[1] | 31.1 |
| 33 | PP/PU 25/75 | 3 | 50 | 26.7 | 79.7 | 49.3 | XMD | 125 | 45.2[1] | 33.8 |
| 33 | PP/PU 50/50 | 3 | 50 | 26.6 | 53.0 | 39.1 | XMD | 125 | 36.1[1] | 32.1 |
| 33 | PP/PU | 3 | 50 | 26.7 | 79.7 | 53.8 | XMD | 125 | 47.3[1] | 35.2 |

TABLE 16-continued

Elastic Recovery Properties of
Polypropylene/Polyurethane (455-200)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | PreAnn. Length (mm) | Post Ann. Length (mm) |
|---|---|---|---|---|---|---|---|---|---|---|
| 3 | PP/PU 50/50 | 5 | 50 | 26.6 | 53.0 | 39.0 | XMD | 125 | 37.0[1] | 33.0 |
| 3 | PP/PU 25/75 | 5 | 50 | 26.7 | 79.7 | 57.9 | XMD | 125 | 53.9[1] | 42.7 |
| 2 | PP/PU 25/75 | 5 | 50 | 26.6 | 53.0 | 42.0 | XMD | 125 | 39.0[1] | 36.0 |
| 2 | PP/PU 50/50 | 5 | 50 | 26.7 | 79.7 | 63.3 | XMD | 125 | 53.2[1] | 49.2 |
| Cntl II | PU 50/50 | — | 50 | 25.4 | 125 | 30.5 | MD | 90 | 30.5 | 26.8 |
| Cntl I | PP | — | 50 | 25.4[2] | — | — | MD | — | — | — |
| 32 | PP/PU 25/75 | 3 | 50 | 26.5 | 79.8 | 51.2 | MD | 90 | 51.2 | 33.5 |
| 32 | PP/PU 25/75 | 3 | 50 | 27.0 | 133.0 | 64.2 | MD | 90 | 64.2 | 36.8 |
| 33 | PP/PU 50/50 | 3 | 50 | 26.5 | 79.8 | 54.1 | MD | 90 | 54.1 | 34.4 |
| 33 | PP/PU 50/50 | 3 | 50 | 27.0 | 133.0 | 77.1 | MD | 90 | 77.1 | 52.3 |
| 3 | PP/PU 25/75 | 5 | 50 | 26.5 | 79.8 | 57.0 | MD | 90 | 57.0 | 42.2 |
| 3 | PP/PU 25/75 | 5 | 50 | 27.0 | 133.0 | 88.4 | MD | 90 | 88.4 | 56.3 |
| 2 | PP/PU 50/50 | 5 | 50 | 26.5 | 79.8 | 63.4 | MD | 90 | 63.4 | 50.3 |
| 2 | PP/PU 50/50 | 5 | 50 | 27.0 | 133.0 | 100.0 | MD | 90 | 100.0 | 77.2 |
| 34 | PP/PU 25/75 | 5 | 75 | 26.5 | 79.8 | 50.3 | MD | 90 | 50.3 | 36.8 |
| 34 | PP/PU 25/75 | 5 | 75 | 27.0 | 133.0 | 87.5 | MD | 90 | 87.5 | 52.5 |
| 6 | PP/PU 25/75 | 5 | 100 | 26.5 | 79.8 | 53.4 | MD | 90 | 53.4 | 39.4 |
| 6 | PP/PU 25/75 | 5 | 100 | 27.0 | 133.0 | 80.0 | MD | 90 | 80.0 | 47.7 |
| 34 | PP/PU 25/75 | 5 | 155 | 26.5 | 79.8 | 54.3 | MD | 90 | 54.3 | 39.4 |
| 34 | PP/PU 25/75 | 5 | 155 | 27.0 | 133.0 | 80.0 | MD | 90 | 80.0 | 47.7 |

[1] A delay of 24 hrs. between measuring the initial recovery length and the annealing experiment allowed further relaxation of the BMF web and additional recovery to occur.
[2] Polypropylene BMF was inelastic and broke on attempted elongation.

TABLE 17

Elastic Recovery Properties of
Polypropylene/Polyurethane (Pellathane 2103-80WC)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | PreAnn. Length (mm) | Post Ann. Length (mm) |
|---|---|---|---|---|---|---|---|---|---|---|
| 36 | PP/PU 25/75 | 3 | 100 | 26.9 | 79.7 | 42.7 | XMD | 90 | 39.2[1] | 37.1 |
| 37 | PP/PU 25/75 | 3 | 190 | 26.9 | 79.7 | 44.8 | XMD | 90 | 39.7[1] | 37.1 |
| 36 | PP/PU 25/75 | 3 | 100 | 26.6 | 53.0 | 34.1 | XMD | 125 | 31.1[1] | 30.1 |
| 36 | PP/PU 25/75 | 3 | 100 | 26.7 | 79.7 | 41.2 | XMD | 125 | 32.8[1] | 32.3 |
| 37 | PP/PU 25/75 | 3 | 190 | 26.6 | 53.0 | 34.1 | XMD | 125 | 31.2[1] | 30.1 |
| 37 | PP/PU 25/75 | 3 | 190 | 26.7 | 79.7 | 42.3 | XMD | 125 | 33.1[1] | 33.1 |
| Cntl VII | PU | — | 100 | 25.4 | 125 | 34.6 | MD | 90 | 34.6 | 28.4 |
| Cntl I | PP | — | 100 | 25.4 | — | — | MD | — | — | — |
| 37 | PP/PU 25/75 | 3 | 100 | 26.5 | 79.8 | 37.9 | MD | 90 | 37.9 | 31.7 |
| 37 | PP/PU 25/75 | 3 | 100 | 27.0 | 133.0 | 46.5 | MD | 90 | 46.5 | 33.7 |
| 38 | PP/PU 25/75 | 5 | 100 | 26.5 | 79.8 | 46.2 | MD | 90 | 46.2 | 37.3 |
| 38 | PP/PU 25/75 | 5 | 100 | 27.0 | 133.0 | 67.1 | MD | 90 | 67.1 | 42.3 |

TABLE 17-continued

Elastic Recovery Properties of
Polypropylene/Polyurethane (Pellathane 2103-80WC)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | PreAnn. Length (mm) | Post Ann. Length (mm) |
|---|---|---|---|---|---|---|---|---|---|---|
| | 25/75 | | | | | | | | | |

[1] A delay of 24 hrs. between measuring the initial recovery length and the annealing experiment allowed further relaxation of the BMF web and additional recovery to occur.
[2] Polypropylene BMF was inelastic and broke on attempted elongation.

TABLE 18

Elastic Recovery Properties of
Polypropylene/Kraton(G-1657)
Elongated/Annealed Webs

| Example | Comp. Polymer/ Ratio | # Layers | Basis Wt. (g/m$_2$) | Init. Length (mm) | Elong. Length (mm) | Rc'vd. Length (mm) | Sample Orient. | Ann. Temp. (°C.) | PreAnn. Length (mm) | Post Ann. Length (mm) |
|---|---|---|---|---|---|---|---|---|---|---|
| 39 | PP/Kraton 37.5/62.5 | 5 | 100 | 26.5 | 79.8 | 51.2 | MD | 90 | 51.2 | 43.2 |
| 39 | PP/Kraton 37.5/62.5 | 5 | 100 | 27.0 | 133.0 | 87.3 | MD | 90 | 87.3 | 73.1 |
| 40 | PP/Kraton 25/75 | 5 | 100 | 26.5 | 79.8 | 40.4 | MD | 90 | 40.4 | 33.6 |
| 40 | PP/Kraton 25/75 | 5 | 100 | 27.0 | 133.0 | 81.5 | MD | 90 | 81.5 | 60.0 |

Example 43

Figure 5:
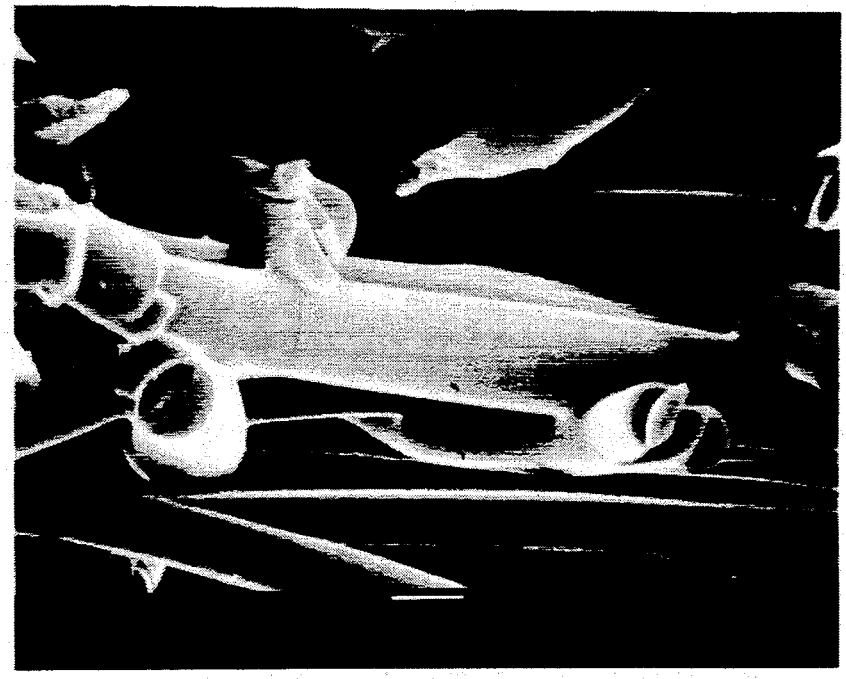
FIGS. 4 and 5 are scanning electron micrographs of web cross sections, for Examples 27 and 43, respectively, prepared by the invention method.

A BMF web was prepared according to the procedure of Example 8 except that the PE and PU melt stream were delivered to a three-layer feedblock. The samples were prepared for SEM analysis as per Example 27 except the PU was not removed, FIG. 5(1000×).

Examples 44–47

Four BMF webs having a basis weight of approximately 100 g/m² and comprising two-layer microfibers having an average diameter of less than about 10 micrometers were prepared according to the procedure of Example 1, except that a 105 MI low-density polyethylene (PE) resin (LLDPE, Aspun TM 6806 available from Dow Chemical Company, Midland, Mich.) was substituted for the polypropylene and a poly(esterurethane) (PU) resin (Morthane TM PS 440-200, available from Morton International, Inc., Seabrook, N.H.) was substituted for the Morthane TM PS 455-200. The extruder temperatures were maintained at 210° C. and 220° C., respectively. The melt streams were delivered to a two-layer feedblock maintained at 220° C. at the pump ratios given in Table 19. The BMF die and primary air supply temperatures were maintained at 220° C. and 221° C., respectively, and the collector distance was 29.6 cm.

A pressure sensitive adhesive suitable for skin adhesion, as described in Example 2 of U.S. Pat. No. 4,871,812 except 0.5% poly(ethyl oxazoline)was added to the adhesive instead of 5%, was coated onto a liner at 7.5 grains per 24 square inches, and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of PE to the elastic PU web improved the heat bond strength over the heat bond strength of the PU web alone (See Control XVI-XIX in Table 20).

Examples 48–51

Four BMF webs having a basis weight of approximately 100 g/m² and comprising two-layer microfibers having an average diameter of less than about 10 micrometers were prepared according to the procedure of Example 1, except that an ethylene vinyl acetate (EVA) copolymer resin (Elvax TM 410 available from E. I. Du Pont de Nemours and Company, Wilmington, Del.) was substituted for the polypropylene and a poly(esterurethane) (PU) resin (Morthane TM PS 440-200, available from Morton International, Inc., Seabrook, N.H.) was substituted for the Morthane TM PS 455-200. The extruder temperatures were maintained at 180° C. and 220° C., respectively. The melt streams were delivered to a two-layer feedblock maintained at 220° C. at the pump ratios given in Table 19. The BMF die and primary air supply temperatures were maintained at 220° C. and 221 ° C., respectively, and the collector distance was 29.6 cm.

A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of EVA to the elastic PU web improved the percent elongation, elastic recovery, and heat bond strength to EVA containing films over the same properties the PU web alone (See Control XVI--XIX in Table 20).

Control Web VIII–XI

Four control webs of the 105 MI low-density polyethylene resin (LLDPE, Aspun TM 6806 available from Dow Chemical Company, Midland, Mich.) were prepared according to the procedure of Example 1, except that only one extruder, which was maintained at 210° C., was used, and it was connected directly to the BMF die through a gear pump. The die and air temperatures were maintained at 210° C. and 218° C., respectively, and the collector distance was 29.6 cm. The resulting BMF webs had the basis weights shown in Table 19 and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The polyethylene webs had lower tensile strength, much lower percent elongation, and less elastic recovery than the polyurethane webs in Control XVI-XIX in Table 20.

Control Webs XII-XV

Four control webs of the ethylene vinyl acetate copolymer resin (Elvax TM 410 available from E. I. Du Pont de Nemours and Company, Wilmington, Del.) were prepared according to the procedure of Example 1, except that only one extruder, which was maintained at 190° C., was used, and it was connected directly to the BMF die through a gear pump. The die and air temperatures were maintained at 190° C. and 192° C., respectively, and the collector distance was 29.6 cm. The resulting BMF webs had the basis weights shown in Table 19 and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20.

The ethylene vinyl acetate webs had lower tensile strength and much lower percent elongation than the polyurethane webs in Control XVI-XIX in Table 20.

Control Web XVI-XIX

Four control webs of the poly(esterurethane) (PU) resin (Morthane TM PS 440-200, available from Morton International, Inc., Seabrook, N.H.) were prepared according to the procedure of Example 1, except that only one extruder, which was maintained at 220° C., was used, and it was connected directly to the BMF die through a gear pump. The die and air temperatures were maintained at 220° C. and 208° C., respectively, and the collector distance was 29.6 cm. The resulting BMF webs had the basis weights shown in Table 19 and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The polyurethane webs had higher tensile strength, higher percent elongation, and higher elastic recovery than the polyethylene or ethylene vinyl acetate webs. The polyurethane webs had sufficient physical properties for use as a tape for ostomy bags. However, polyurethane webs did not have sufficient heat bonding strength to the Cryovac MF 375 film.

Control XX

A polyurethane:polypropylene commingled BMF web of the present invention was prepared using a melt blowing process similar to that described in Example 1, except that the BMF apparatus utilized two extruders and two dies. The dies were angled such that the stream of fibers from each die collide and commingle before they are collected on the collector (See FIG. 1b). The first extruder (240° C.) delivered a melt stream of a 400 melt flow rate (MFR) polypropylene (PP) resin (Exxon 3505G, available from Exxon Chemical Company, Baytown, Tex.) to the first die (225° C.). The second extruder (230° C.) delivered a melt stream of a poly(esterurethane) (PU) resin (Morthane TM PS 440-200, available from Morton International, Inc., Seabrook, N.H.) to the second die (approximately 225° C.). The gear pumps were adjusted so that a 80:20 ratio percent PP:PU polymer melt was delivered to the dies. The primary air supply temperature was maintained at approximately 283° C. The web was collected at a collector to die distance of approximately 15.2 cm. The resulting commingled BMF web had a basis weight of 100 g/m² and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of PP to the elastic PU web improved the tensile strength, percent elongation, and force values over the same properties of the PU web alone (See Control XVI-XIX in Table 20). However, the heat bonding strength to the Cryovac MF film was inadequate. It is presently believed that a higher heat bonding temperature is needed for this particular web. In addition, a greater melting temperature difference is preferred between the two microfiber materials.

Control XXI

A polyurethane:nylon 6 commingled BMF web of the present invention was prepared using a melt blowing process similar to that described in Example 1, except that the BMF apparatus was arranged as in Control XX. The first extruder (300° C.) delivered a melt stream of a low viscosity nylon 6 resin (BASF KR4405, available from BASF Chemical Company, Parsippany N.J.) to the first die (290° C.). The second extruder (230° C.) delivered a melt stream of a poly(esterurethane) (PU) resin (Morthane TM PS 440-200, available from Morton International, Inc., Seabrook, N.H.) to the second die (approximately 225° C.). The gear pumps were adjusted so that a 20:80 ratio percent nylon 6:PU polymer melt was delivered to the dies. The primary air supply temperature was maintained at approximately 298° C. The web was collected at a collector to die distance of approximately 15.2 cm. The resulting commingled BMF web had a basis weight of 100 g/m² and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of nylon 6 to the elastic PU web improved the tensile strength and force values over the same properties of the PU web alone (See Control XVI--XIX in Table 20). However, the heat bonding strength to the Cryovac MF film was inadequate. It is presently believed that a higher heat bonding temperature is needed for this particular web.

Example 52

A polyurethane:polyethylene commingled BMF web of the present invention was prepared using a melt blowing process similar to that described in Example 1, except that the BMF apparatus was arranged as in Control XX. The first extruder (315° C.) delivered a melt stream of a polyethylene resin having a melt index of 125 (Dow 6814, available from Dow Chemical Company, Midland, Mich.) to the first die (252° C.). The second extruder (230° C.) delivered a melt stream of a poly(esterurethane) (PU) resin (Morthane ™ PS 440-200, available from Morton International, Inc., Seabrook, N.H.) to the second die (approximately 225 ° C.). The gear pumps were adjusted so that a 80:20 ratio percent PU:Polyethylene polymer melt was delivered to the dies. The primary air supply temperature was maintained at approximately 284° C. The web was collected at a collector to die distance of approximately 15.2 cm. The resulting commingled BMF web had a basis weight of 100 g/m$^2$ and an average fiber diameter of less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of PE to the elastic PU web improved the heat bond strength, tensile strength, percent elongation and force values over the same properties of the PU web alone (See Control XVI–XIX in Table 20).

Examples 53 and 54

Two BMF webs were prepared using the process described in U.S. Pat. No. 4,118,531 and as described by FIG. 1c of the present invention. As the blown microfibers were leaving the die, staple PE fibers (Hercules Product Type 201, 3 denier, 4.76 cm long available from Hercules Inc., Norcross, Ga.) were mixed in the stream of BMF. The BMF were prepared from a poly(esterurethane) (PU) resin (Morthane ™ PS 440-200, available from Morton International, Inc., Seabrook, N.H.). The extruder temperature was maintained at approximately 225° C., the BMF die and primary air supply temperature was maintained at 225° C. and 234° C., respectively, and the collector distance was 33 cm. The resulting mixed staple and BMF web had a basis weight and a ratio of staple PE fiber to PU as shown in Table 19. The average fiber diameter of the BMF was less than about 10 micrometers. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The addition of staple PE fibers to the elastic PU web, as in Example 53, improved the heat bond strength, tensile strength, percent elongation and force values over the same properties of the PU web alone (See Control XXII in Table 20).

Control XXII

One BMF web was prepared using the same process as described for Examples 53 and 54 except the staple PE fibers were omitted for the purpose of comparison. A pressure sensitive adhesive suitable for skin adhesion, as described in Examples 44–47 was coated on a liner and laminated to the webs. The adhesive laminated webs were tested for tensile strength, percent elongation, force value at 5, 10, and 25 percent elongation, elastic recovery, moisture vapor transmission rate, and heat bond strength. The results of these tests are shown in Table 20. The properties of this PU web were similar to Control XVI-XIX.

TABLE 19

| Example No. | BMF Process | Basis Weight (g/m$^2$) | Pump Ratio | Composition Resin 1:Resin 2 (%:%) |
|---|---|---|---|---|
| 44 | two-layer | 102 | 20:80 | PU:PE |
| 45 | two-layer | 100 | 40:60 | PU:PE |
| 46 | two-layer | 102 | 60:40 | PU:PE |
| 47 | two-layer | 100 | 80:20 | PU:PE |
| 48 | two-layer | 100 | 20:80 | PU:EVA |
| 49 | two-layer | 99 | 40:60 | PU:EVA |
| 50 | two-layer | 99 | 60:40 | PU:EVA |
| 51 | two-layer | 100 | 80:20 | PU:EVA |
| Control VIII | one-layer | 20 | 100 | PE |
| Control IX | one-layer | 41 | 100 | PE |
| Control X | one-layer | 60 | 100 | PE |
| Control XI | one-layer | 81 | 100 | PE |
| Control XII | one-layer | 20 | 100 | EVA |
| Control XIII | one-layer | 40 | 100 | EVA |
| Control XIV | one-layer | 59 | 100 | EVA |
| Control XV | one-layer | 82 | 100 | EVA |
| Control XVI | one-layer | 20 | 100 | PU |
| Control XVII | one-layer | 40 | 100 | PU |
| Control XVIII | one-layer | 61 | 100 | PU |
| Control XIX | one-layer | 80 | 100 | PU |
| Control XX | commingled | 100 | 80:20 | PU:PP |
| Control XXI | commingled | 100 | 80:20 | PU:Nylon 6 |
| 52 | commingled | 100 | 80:20 | PU:PE |
| Control XXII | BMF | 100 | 100 | PU |
| 53 | BMF + staple | 100 | 50:50 | PU:PE |
| 54 | BMF + staple | 50 | 80:20 | PU:PE |

TABLE 20

| Example No. | Heat Bonding Temperature (°C.) | "T" Peel (N/cm) | Notes: c, wd, w | Tensile Strength (N/cm) | Elongation at break (%) | F5 (N) | F10 (N) | F25 (N) | Elastic Recovery (%) | | MVTR (g m$^{-2}$ 24 hours$^{-1}$) |
|---|---|---|---|---|---|---|---|---|---|---|---|
| | | | | | | | | | MD | CD | |
| 44 | 135 | 1.13 | w | 1.93 | 113 | 0.44 | 0.89 | 2.80 | 61 | 62 | 2032 |
| 45 | 121 | 1.20 | w | 1.75 | 180 | 0.44 | 0.89 | 2.36 | 59 | 66 | 1554 |
| 46 | 135 | 2.41 | w | 1.98 | 278 | 0.89 | 1.91 | 2.80 | 77 | 78 | 3018 |
| 47 | 135 | 1.82 | w | 2.28 | 350 | 0.71 | 1.33 | 2.49 | 89 | 73 | 2523 |
| 48 | 121 | 4.63 | w | 5.13 | 453 | 1.78 | 3.56 | 5.78 | 87 | 83 | 1289 |
| 49 | 121 | 3.35 | c | 7.18 | 478 | 1.47 | 2.94 | 5.34 | 83 | 84 | 2672 |
| 50 | 121 | 2.77 | w | 8.34 | 485 | 1.60 | 3.25 | 5.34 | 85 | 87 | 1755 |

TABLE 20-continued

| Example No. | Heat Bonding Temperature (°C.) | "T" Peel (N/cm) | Notes: c, wd, w | Tensile Strength (N/cm) | Elongation at break (%) | F5 (N) | F10 (N) | F25 (N) | Elastic Recovery (%) MD | Elastic Recovery (%) CD | MVTR (g m$^{-2}$ 24 hours$^{-1}$) |
|---|---|---|---|---|---|---|---|---|---|---|---|
| 51 | 121 | 0.77 | c | 7.53 | 463 | 1.02 | 2.22 | 4.27 | 86 | 75 | 2362 |
| Control VIII | 135 | 1.06 | w | 1.05 | 185 | 0.71 | 1.16 | 1.78 | 61 | 59 | 1910 |
| Control IX | 135 | 0.94 | w | 1.33 | 143 | 0.71 | 1.38 | 2.49 | 56 | 59 | 3404 |
| Control X | 135 | 0.83 | w | 1.80 | 120 | 0.58 | 1.38 | 3.38 | 72 | 62 | 1857 |
| Control XI | 135 | 0.73 | w | 1.98 | 93 | 0.71 | 1.60 | 3.69 | 72 | 63 | 1593 |
| Control XII | 121 | 0.72 | w | 0.58 | 197 | 0.22 | 0.36 | 0.80 | 77 | 90 | 3762 |
| Control XIII | 121 | 1.35 | w | 1.23 | 142 | 0.44 | 0.93 | 1.78 | 88 | 90 | 3823 |
| Control XIV | 121 | 1.97 | w | 1.75 | 135 | 0.27 | 0.89 | 2.67 | 94 | 91 | 3976 |
| Control XV | 121 | 2.15 | w | 2.28 | 105 | 1.16 | 2.09 | 4.00 | 91 | 90 | 3265 |
| Control XVI | 204 | 0.25 | c | 3.50 | 358 | 0.44 | 0.80 | 1.47 | 89 | 78 | 2995 |
| Control XVII | 204 | 0.58 | c | 5.43 | 432 | 0.58 | 1.02 | 1.78 | 90 | 93 | 2486 |
| Control XVIII | 204 | 0.94 | c | 6.65 | 355 | 0.58 | 1.16 | 2.49 | 87 | 93 | 3585 |
| Control XIX | 204 | 0.77 | c | 7.88 | 383 | 1.16 | 2.05 | 3.38 | 93 | 94 | 2032 |
| Control XX | 135 | 1.82 | c | 8.23 | 423 | 9.03 | 11.56 | 12.90 | 83 | 81 | 1418 |
| Control XXI | 135 | 1.35 | c | 14.13 | 352 | 5.78 | 11.56 | 17.57 | 76 | 81 | 4302 |
| 52 | 135 | 2.77 | c | 12.63 | 478 | 2.05 | 4.71 | 9.47 | 82 | 83 | 3891 |
| Control XXII | 177 | 0.99 | c | 6.48 | 348 | 0.44 | 0.89 | 1.78 | 94 | 87 | 1742 |
| 53 | 177 | 3.57 | wd | 1.23 | 172 | 0.22 | 0.36 | 0.53 | 88 | 81 | 1236 |
| 54 | 177 | 0.99 | c | 1.14 | 224 | 0.22 | 0.40 | 0.53 | 90 | 79 | 1498 | c = complete separation
w = web broke
wd = web delamination

The various modifications and alterations of this invention will be apparent to those skilled in the art without departing from the scope and spirit of this invention and this invention should not be restricted to that set forth herein for illustrative purposes.

What is claimed is:

1. An ostomy appliance, comprising:
   a bag having an opening for receiving material from a stoma;
   an elastomeric medical tape comprising an extensible nonwoven web comprising a mixture of an elastomeric meltblown microfiber and a heat bondable material, wherein said tape has a bag side and a skin side, wherein said bag side of the tape has an inner portion capable of being heat or sonically bonded to said bag circumscribing the opening and an outer portion which is adapted to be supported on the user's skin with the bag side exposed to the air; and
   a layer of pressure sensitive adhesive on the skin side of the tape for attaching the tape to the peristomal area of the user.

2. An ostomy appliance according to claim 1, wherein said tape has a moisture vapor transmission rate at least 500 g m$^{-2}$ 24 hrs$^{-1}$.

3. An ostomy appliance according to claim 1, wherein the heat bondable material is selected from the group consisting of ethylene copolymers, ethylene polymers and ethylene vinyl acetate copolymers.

4. An ostomy appliance according to claim 1, wherein the elastomeric microfiber comprises a polyurethane.

5. An ostomy appliance according to claim 1, wherein the heat bondable material is selected from the group consisting of melt blown multilayered microfibers, melt blown monolayer microfibers, and staple fibers.

6. An ostomy appliance according to claim 1, wherein said inner portion is directly heat sealed to said bag circumscribing the opening.

7. An ostomy appliance according to claim 1, wherein said tape is capable of being heat or sonically bonded to a polymer substrate selected from the group consisting of polyethylene-based polymers and polyethylene-based copolymers.

8. An ostomy appliance according to claim 1, wherein the average fiber diameter is less than about 10 micrometers.

9. An ostomy appliance, comprising:
   a bag having an opening for receiving material from a stoma; and
   an elastomeric medical tape, comprising: an extensible nonwoven web comprising meltblown microfibers each of said microfibers having at least two substantially continuous layers throughout said microfiber length comprised of at least one first layer of an elastomeric material and at least one second layer of a heat bondable material; and a layer of pressure sensitive adhesive on at least one face of said web, wherein said medical tape has an extensibility of at least 100% and said bag side of the tape has an inner portion capable of being heat or sonically bonded to said bag circumscribing the opening and an outer portion which is adapted to be supported on the user's skin with the bag side exposed to the air.

10. An ostomy appliance according to claim 9, wherein said tape is capable of being heat or sonically bonded to a polymer substrate selected from the group consisting of polyethylene-based polymers and polyethylene-based copolymers.

11. An ostomy appliance according to claim 9, wherein the elastomeric material has a heat bonding temperature at least 15 degrees centigrade higher than said heat bondable material.

12. An ostomy appliance according to claim 9, wherein the layers of said microfibers are concentrically layered.

13. An ostomy appliance according to claim 12, wherein an outer sheath layer comprises a heat or sonic bonding layer with at least one internal core layer of an elastomeric material.

14. An ostomy appliance according to claim 9, wherein the layers of said microfibers are longitudinally layered.

15. An ostomy appliance according to claim 9, wherein the average fiber diameter is less than about 10 micrometers.

16. An ostomy appliance, comprising:
a bag having an opening for receiving material from a stoma; and
an elastomeric medical tape, comprising: an extensible nonwoven web comprising meltblown microfibers each of said microfibers having at least two substantially continuous layers throughout said microfiber length comprised of at least one first layer of an elastomeric material and at least one second layer of a heat bondable material; and a layer of pressure sensitive adhesive on at least one face of said web, wherein said medical tape has an extensibility of at least 100% and said bag side of the tape has an inner portion capable of being heat or sonically bonded to a snap ring adapted to engage a complementary snap ring bonded to said bag and an outer portion which is adapted to be supported on the user's skin with the bag side exposed to the air.

* * * * *

UNITED STATES PATENT AND TRADEMARK OFFICE
CERTIFICATE OF CORRECTION

PATENT NO. : 5,423,783
DATED : June 13, 1995
INVENTOR(S) : Donald R. Battles, Eugene G. Joseph, Audrey S. Huang, John F. Reed and Scott M. Purrington It is certified that error appears in the above-indentified patent and that said Letters Patent is hereby corrected as shown below:

Col. 2, line 35, "tier" should read -- for --.

Col. 2, line 40, "there/ore" should read -- therefore --.

Col. 2, line 59, "or" should read -- for --.

Col. 18, line 65, "toil" should read -- foil --.

Col. 27, line 53, "g/m:" should read -- $g/m^2$ --.

Signed and Sealed this

Fifth Day of March, 1996

*Attest:*

BRUCE LEHMAN

*Attesting Officer*      *Commissioner of Patents and Trademarks*